(12) United States Patent
Ogilvie et al.

(10) Patent No.: US 8,297,275 B2
(45) Date of Patent: Oct. 30, 2012

(54) ADJUSTABLE ORAL AIRWAY DEVICES, AND ADJUSTABLE ORAL AIRWAY KITS

(76) Inventors: Daniel Ogilvie, Spokane, WA (US); Beata Zawadzka, Spokane, WA (US)

( * ) Notice: Subject to any disclaimer, the term of this patent is extended or adjusted under 35 U.S.C. 154(b) by 869 days.

(21) Appl. No.: 12/409,022

(22) Filed: Mar. 23, 2009

(65) Prior Publication Data

US 2010/0095968 A1 Apr. 22, 2010

Related U.S. Application Data

(60) Provisional application No. 61/106,875, filed on Oct. 20, 2008.

(51) Int. Cl.
*A61M 16/00* (2006.01)
(52) U.S. Cl. .......... 128/200.26; 128/207.14; 128/200.24
(58) Field of Classification Search ............. 128/200.26, 128/200.24, 207.14, 861
See application file for complete search history.

(56) References Cited

U.S. PATENT DOCUMENTS

| | | | |
|---|---|---|---|
| 3,774,616 A * | 11/1973 | White et al. ............. | 128/200.26 |
| 3,930,507 A | 1/1976 | Berman | |
| 4,068,658 A | 1/1978 | Berman | |
| 4,112,936 A | 9/1978 | Blachly | |
| 4,365,625 A | 12/1982 | Rind | |
| 4,919,126 A | 4/1990 | Baildon | |
| 5,421,327 A * | 6/1995 | Flynn et al. ............. | 128/207.17 |
| 5,590,643 A | 1/1997 | Flam | |
| 5,740,791 A * | 4/1998 | Aves ......................... | 128/200.26 |
| 6,386,199 B1 | 5/2002 | Alfery | |
| 2008/0156324 A1* | 7/2008 | Isenberg et al. .......... | 128/200.26 |

* cited by examiner

*Primary Examiner* — Lynne Anderson
*Assistant Examiner* — Bradley Philips
(74) *Attorney, Agent, or Firm* — Wells St. John P.S.

(57) ABSTRACT

Some embodiments include adjustable oral airway devices. The devices may contain a bite block, a tongue deflector extending through the bite block, and at least one locking mechanism configured for releasably retaining the tongue deflector in one of two or more predetermined positions within the bite block. Some embodiments include adjustable oral airway kits. Such kits may contain a bite block, a tongue deflector configured to extend within an opening in the bite block, and at least one locking mechanism configured for releasably retaining the tongue deflector in one of two or more predetermined positions within the bite block.

12 Claims, 21 Drawing Sheets

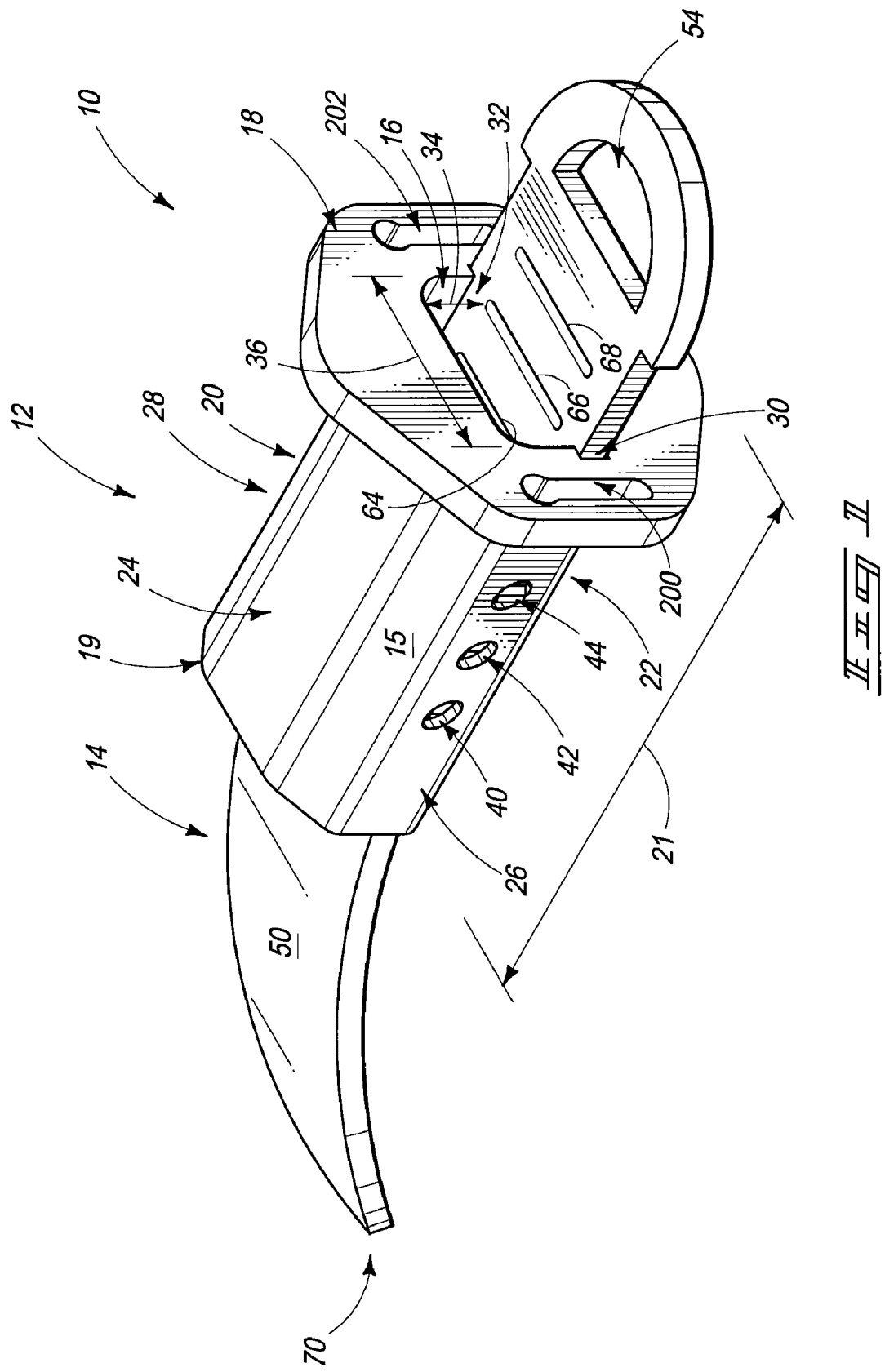

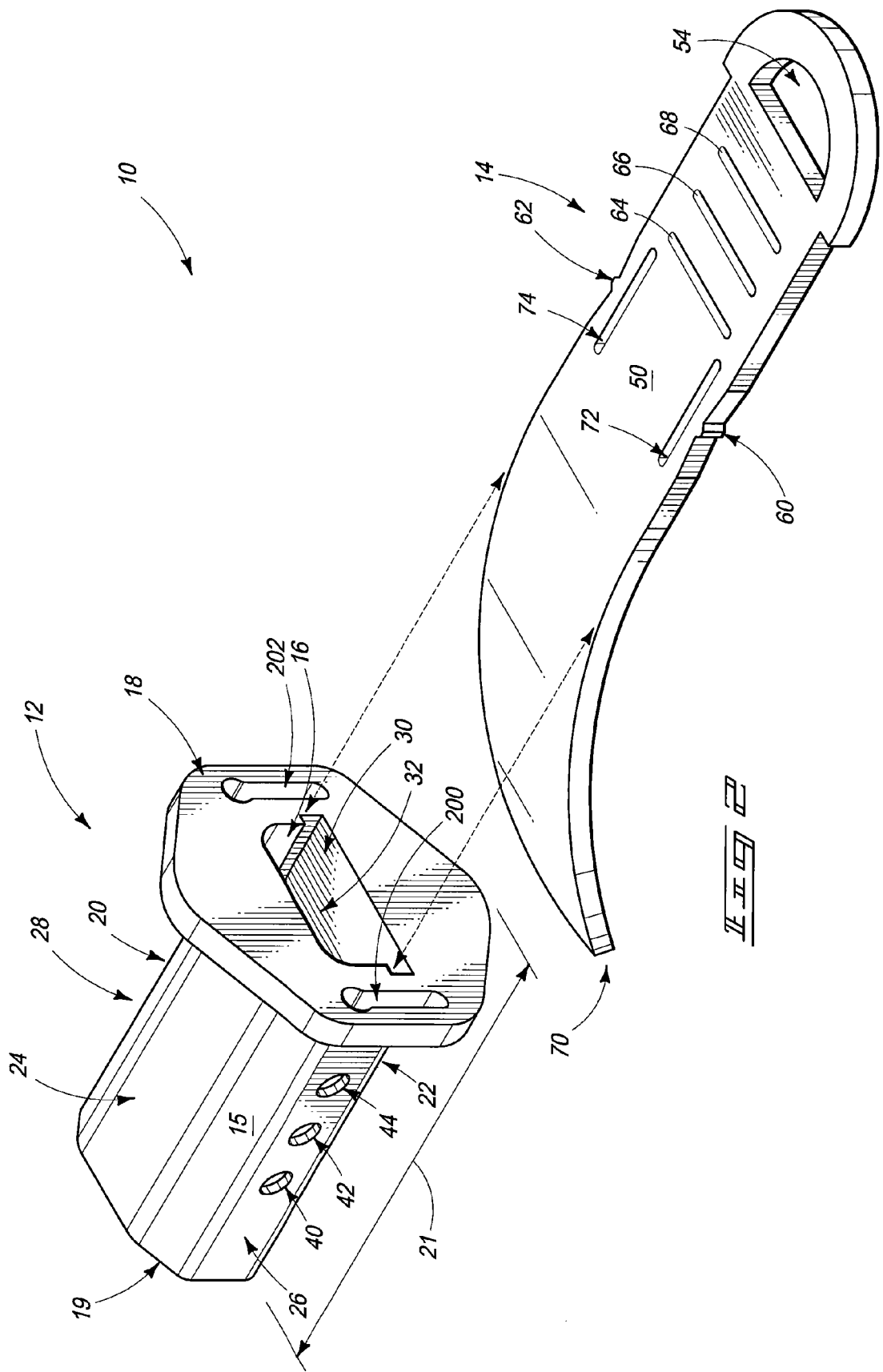

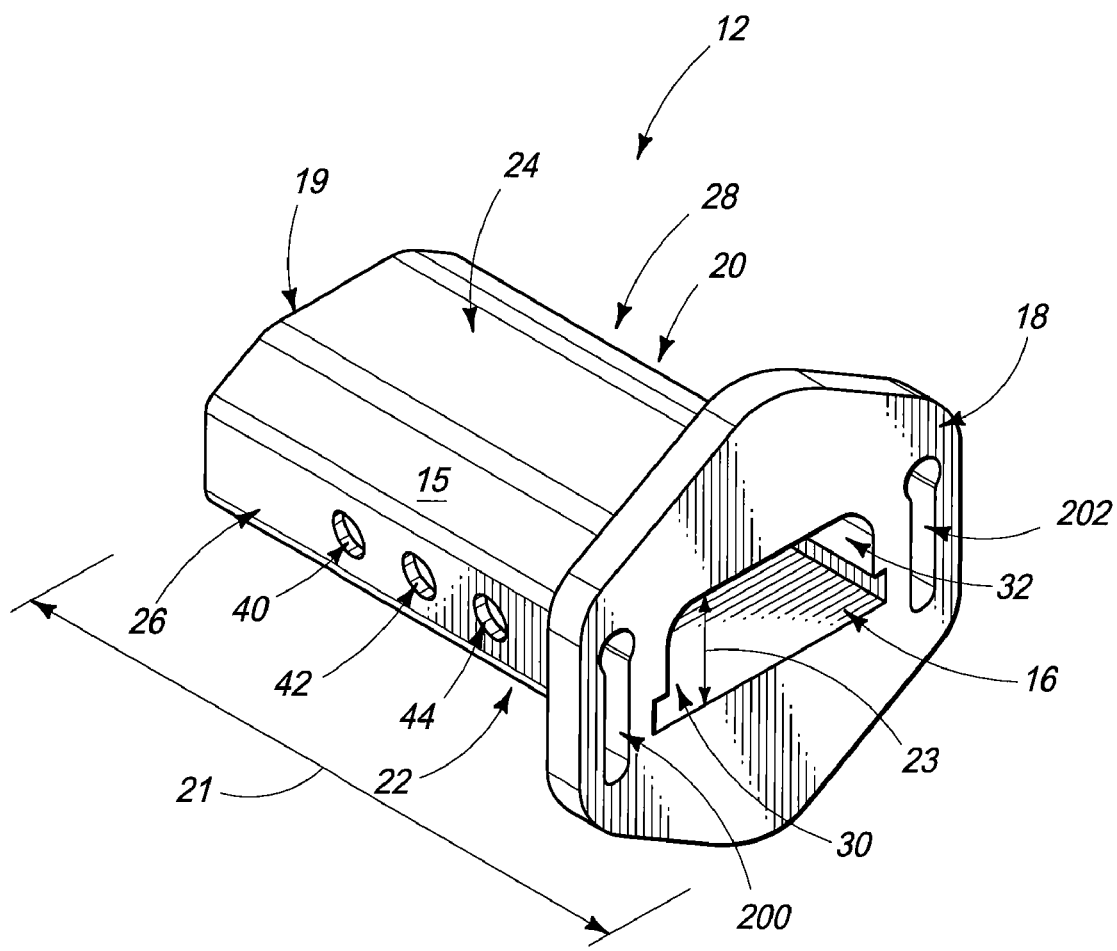

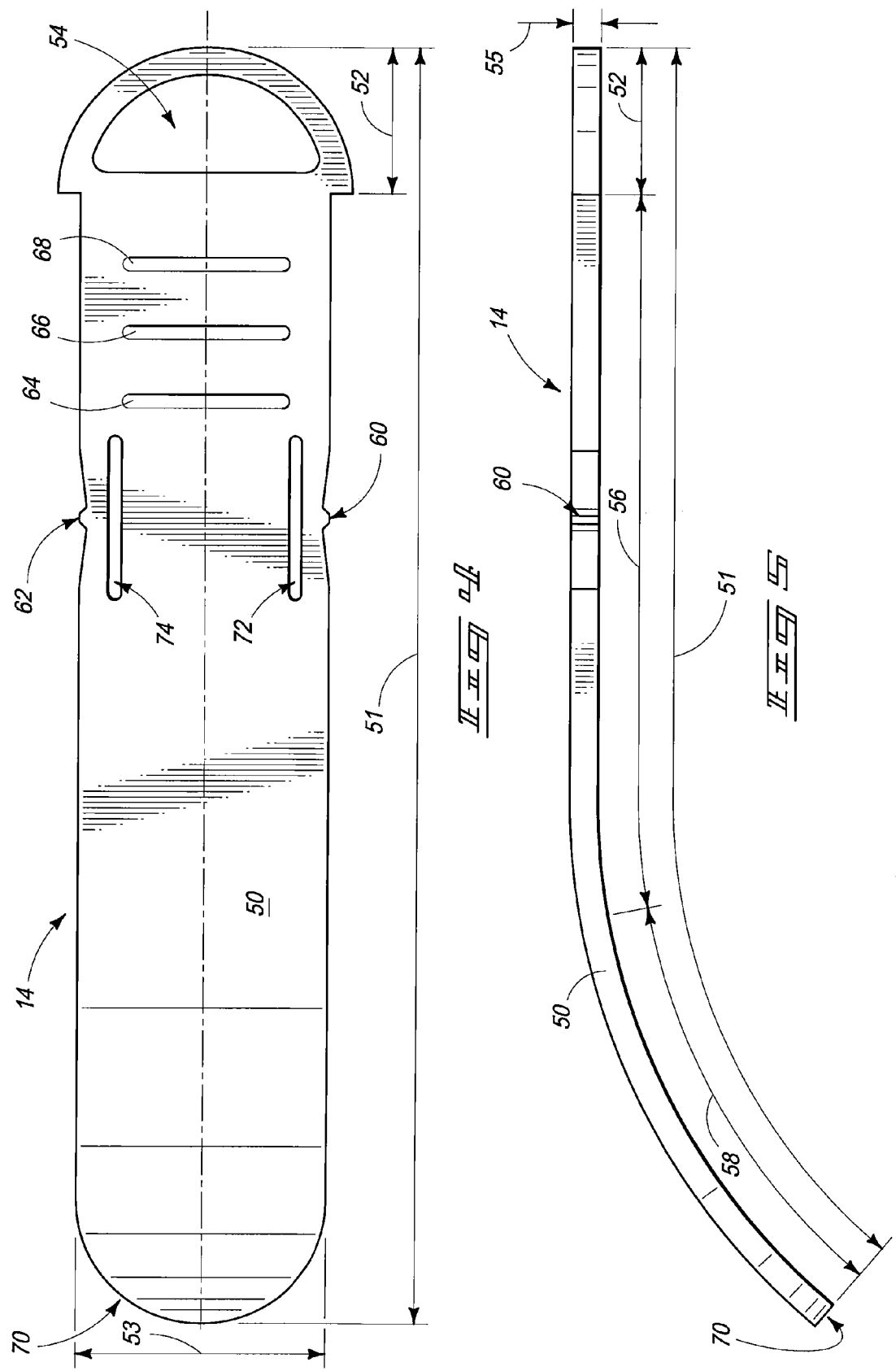

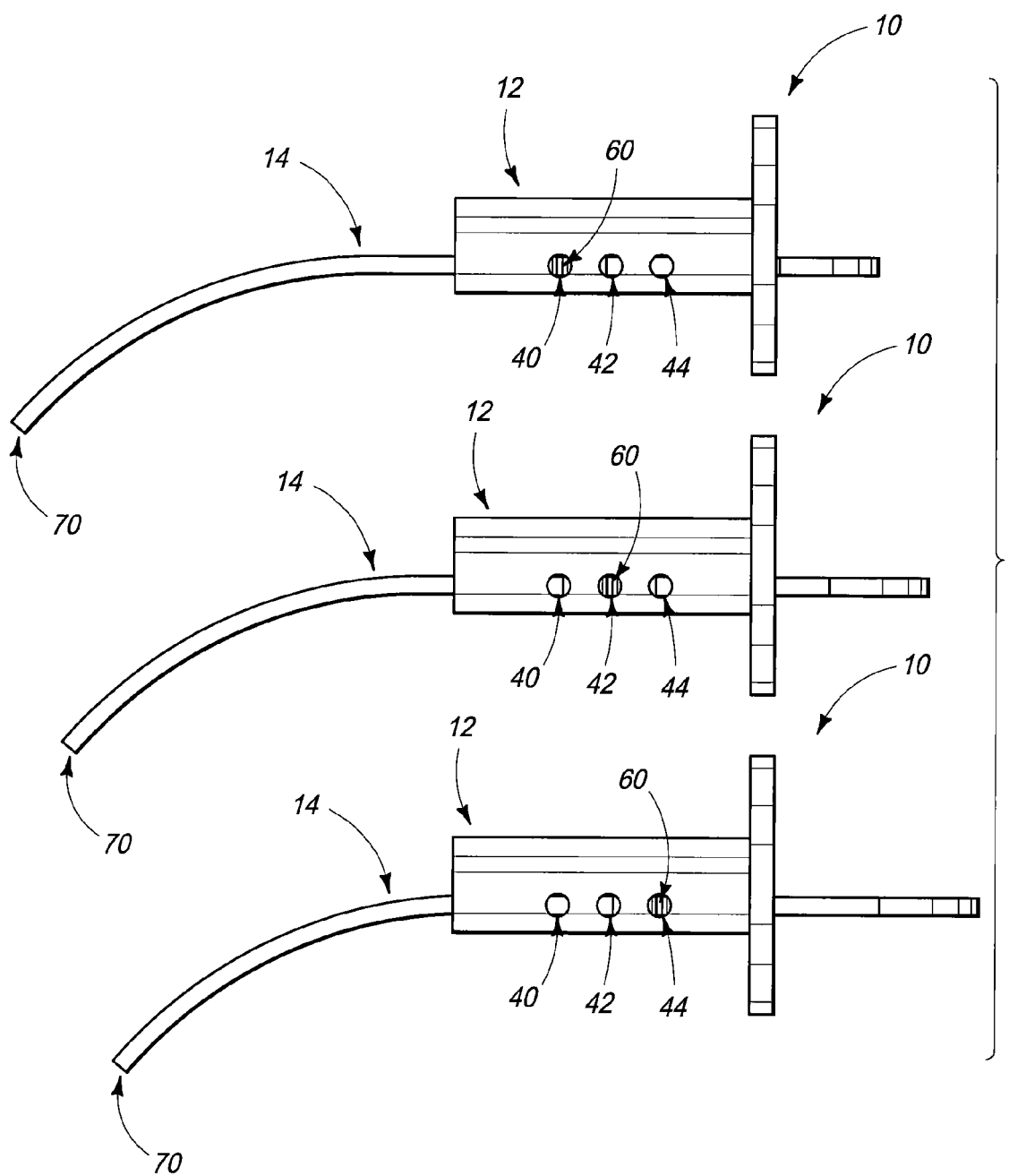

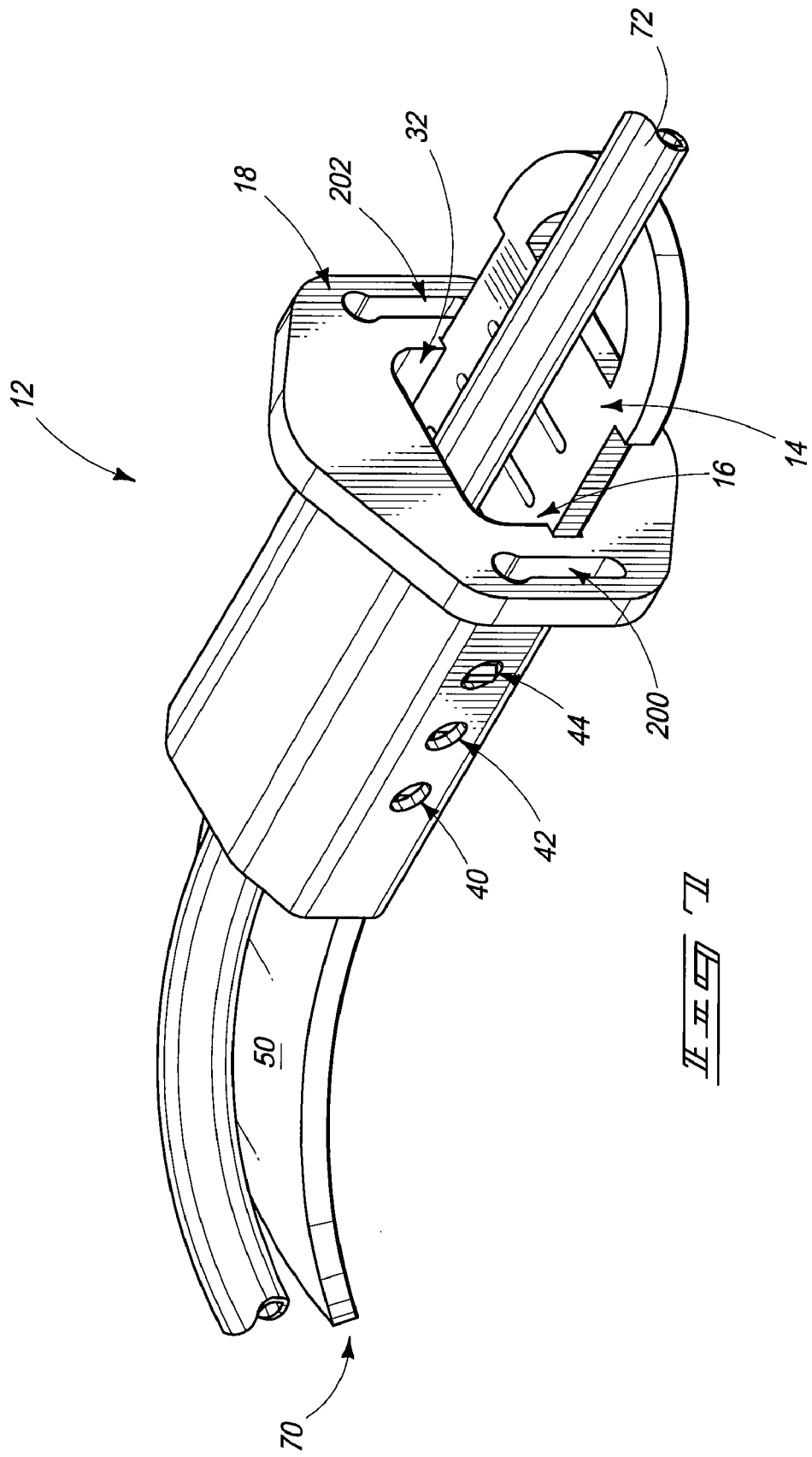

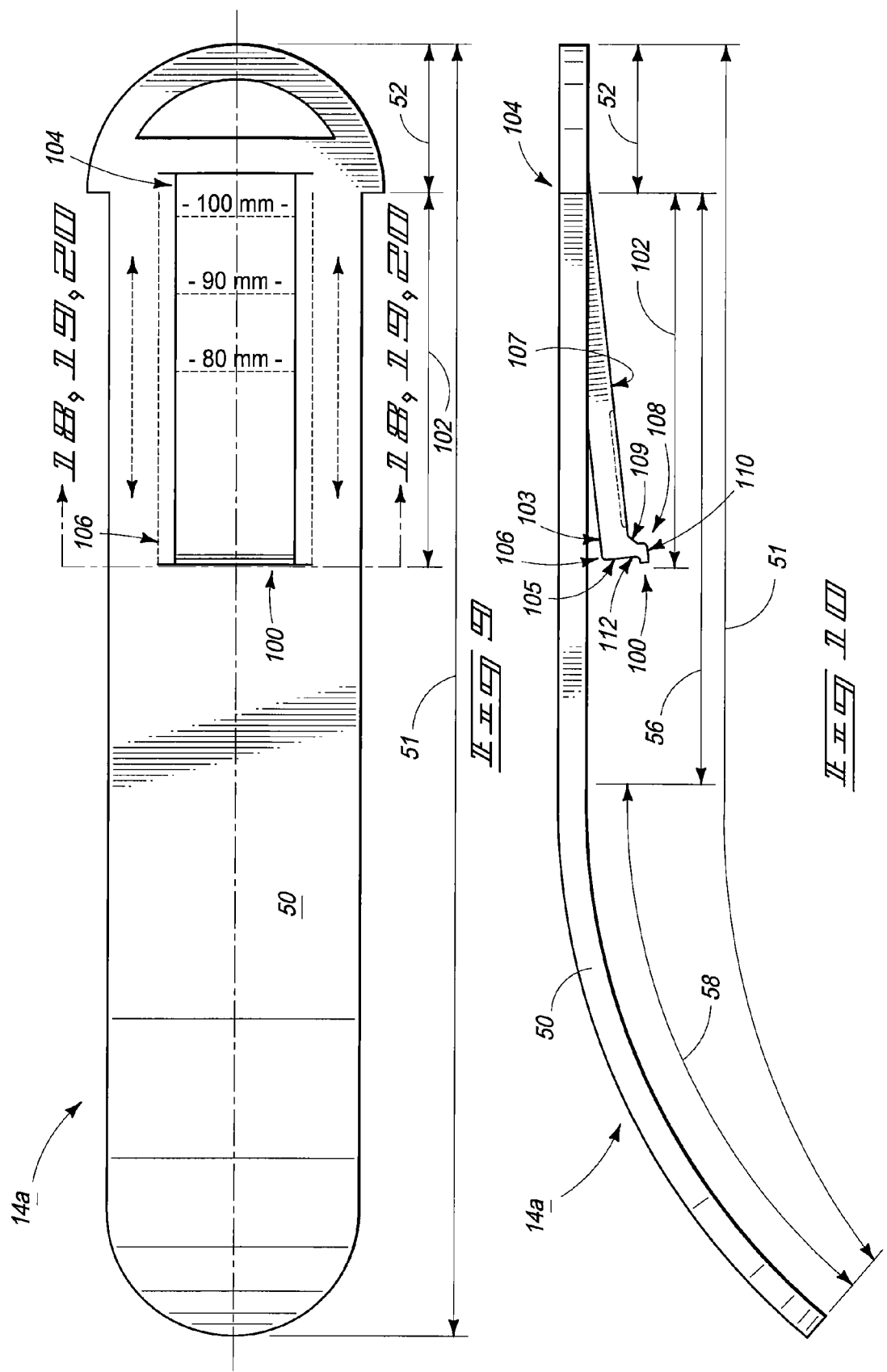

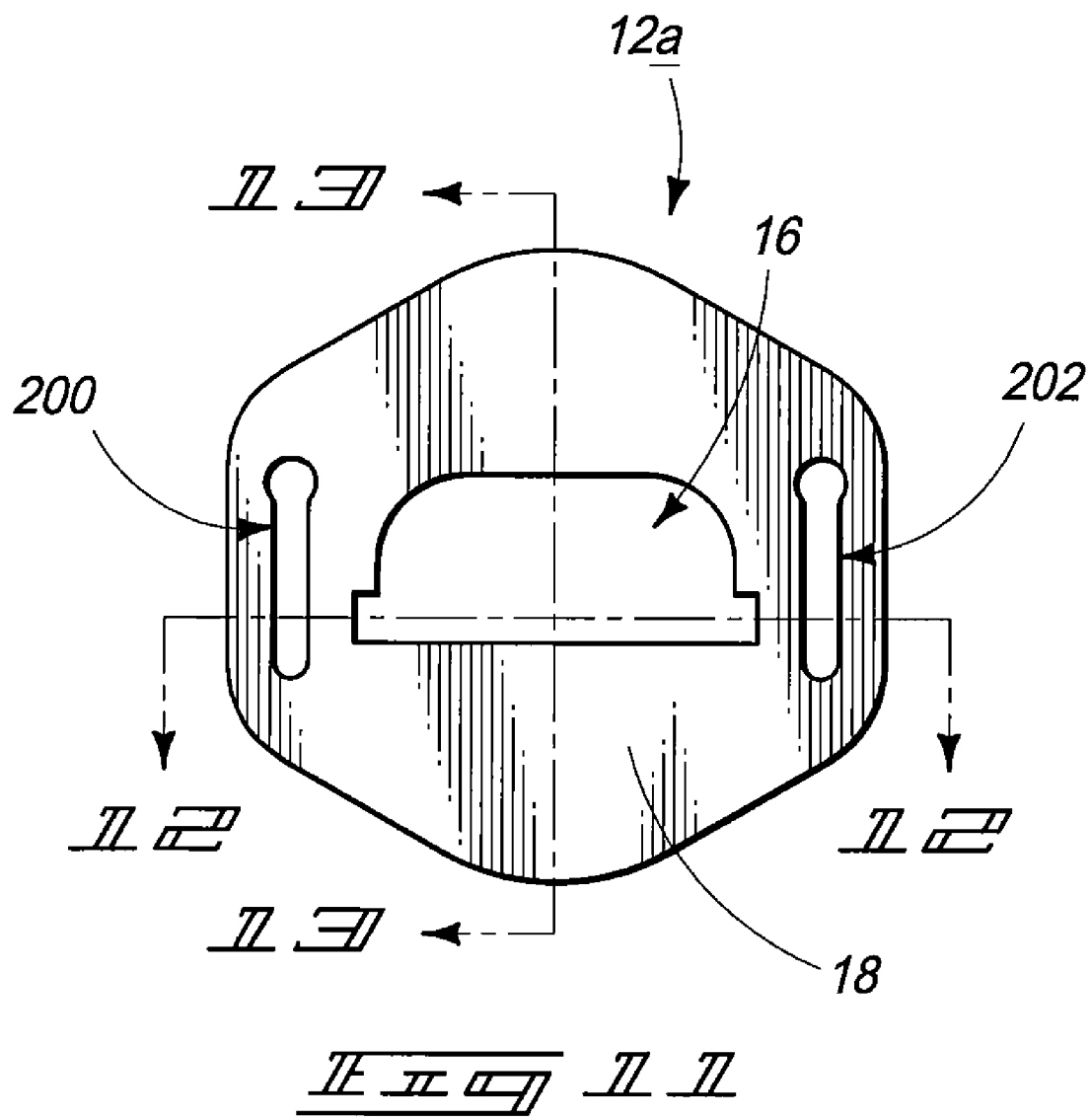

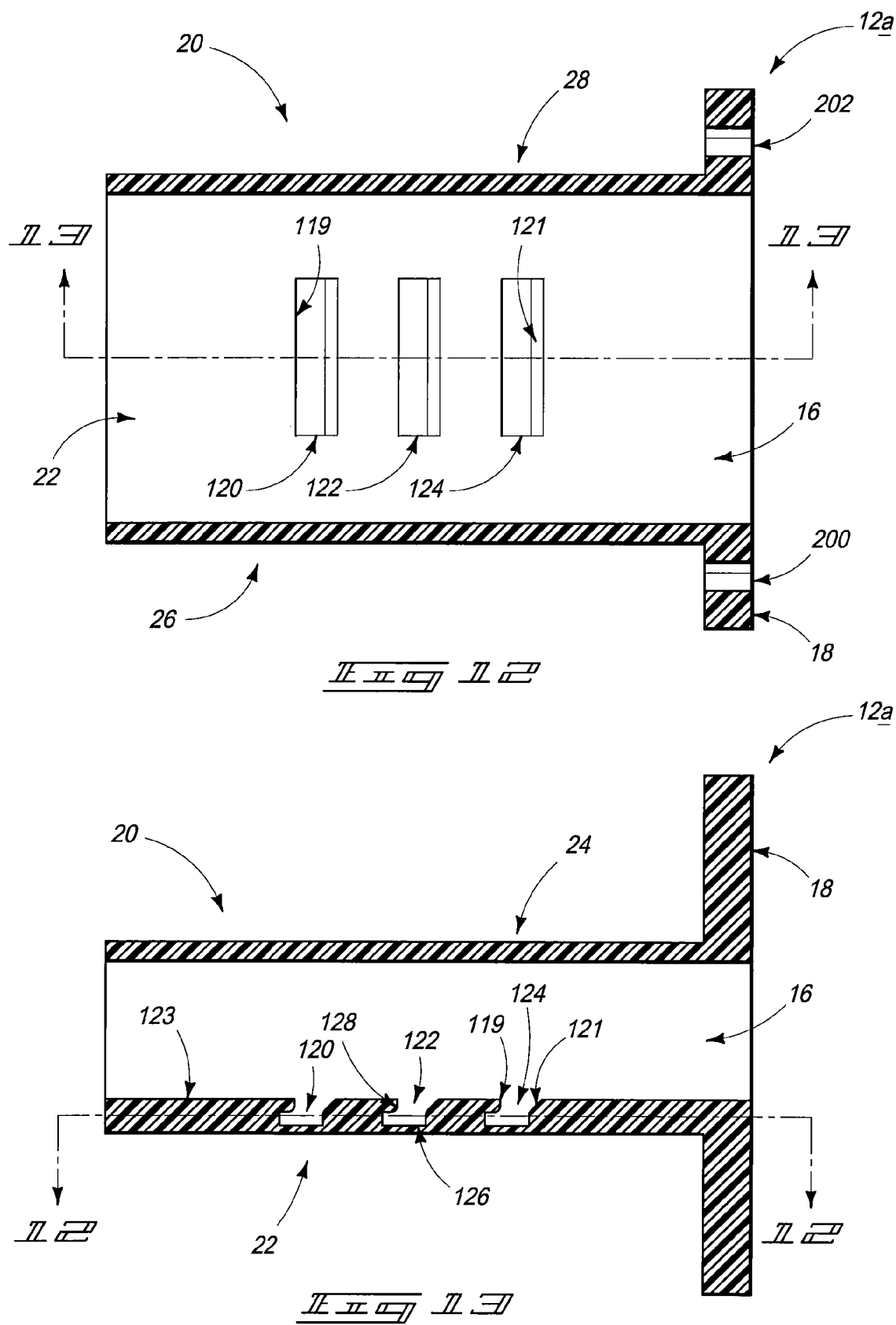

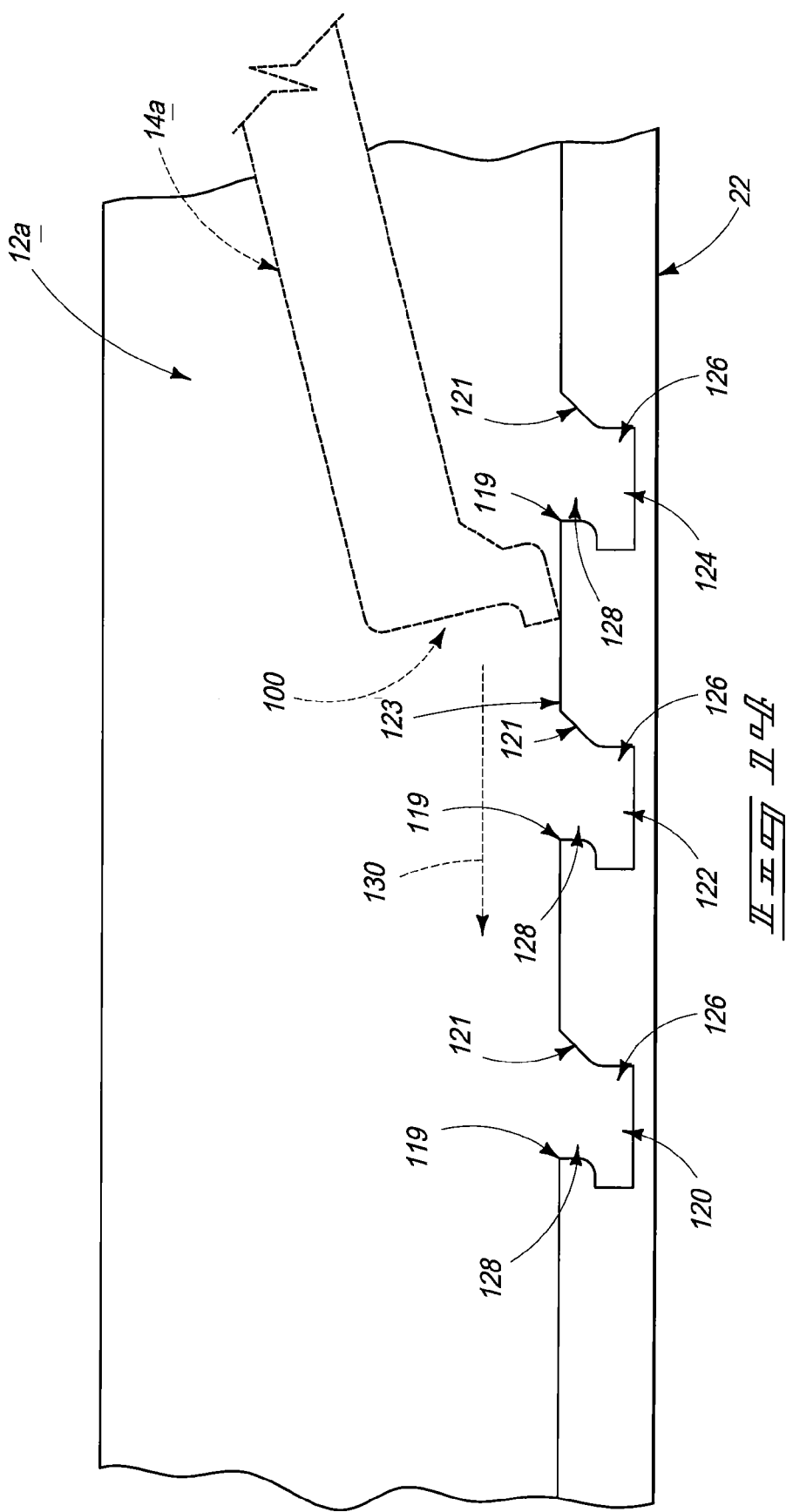

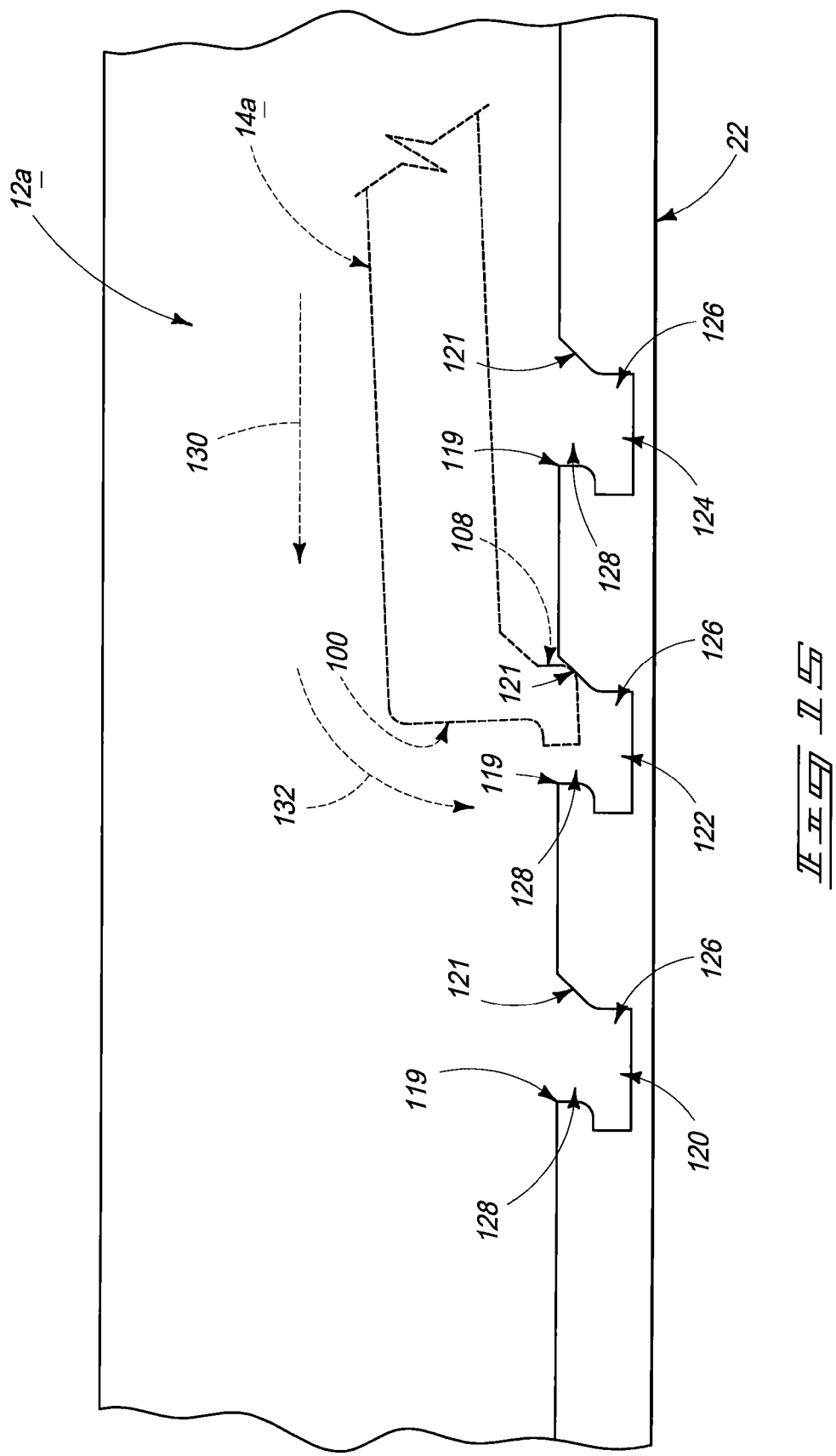

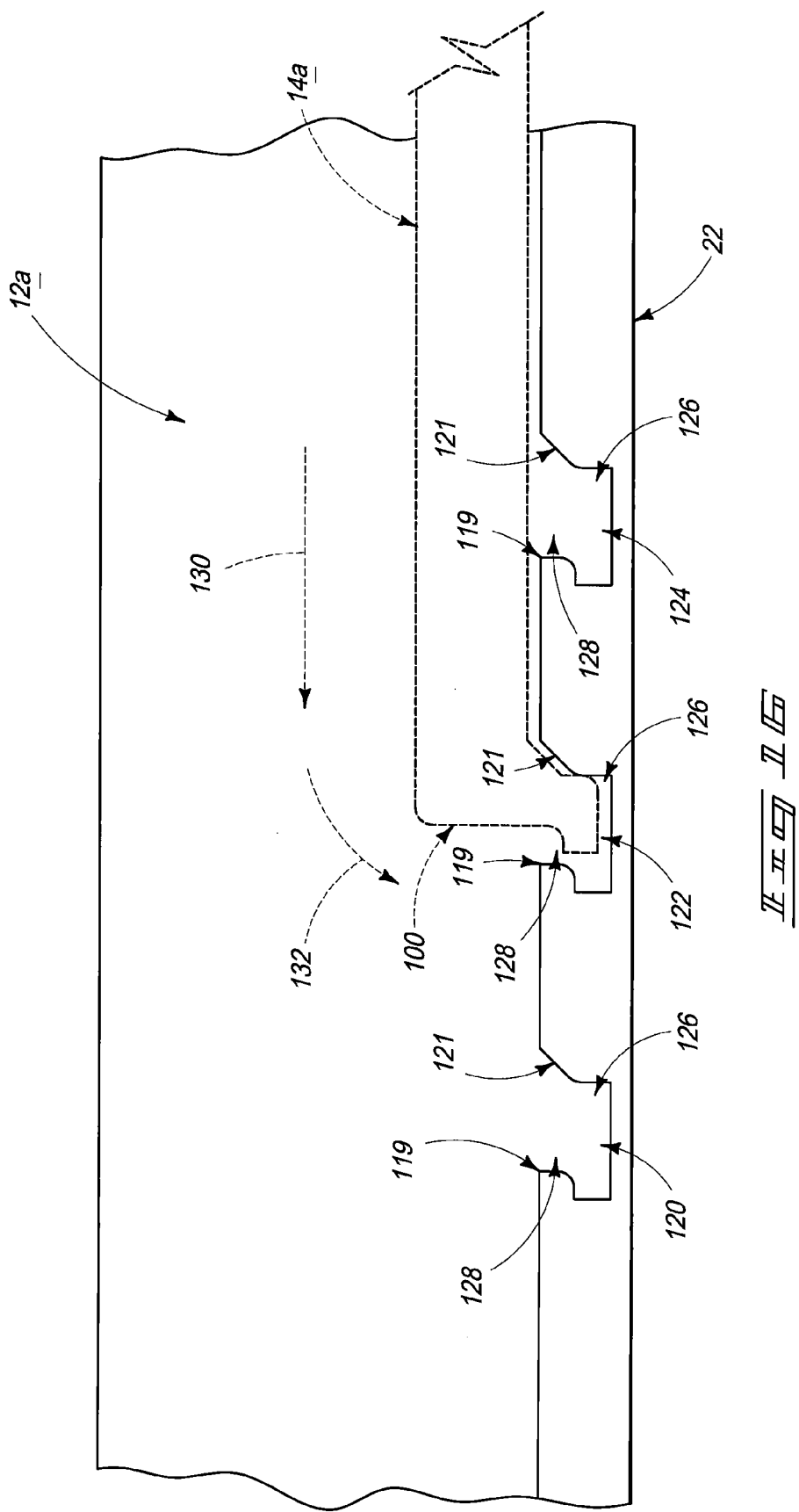

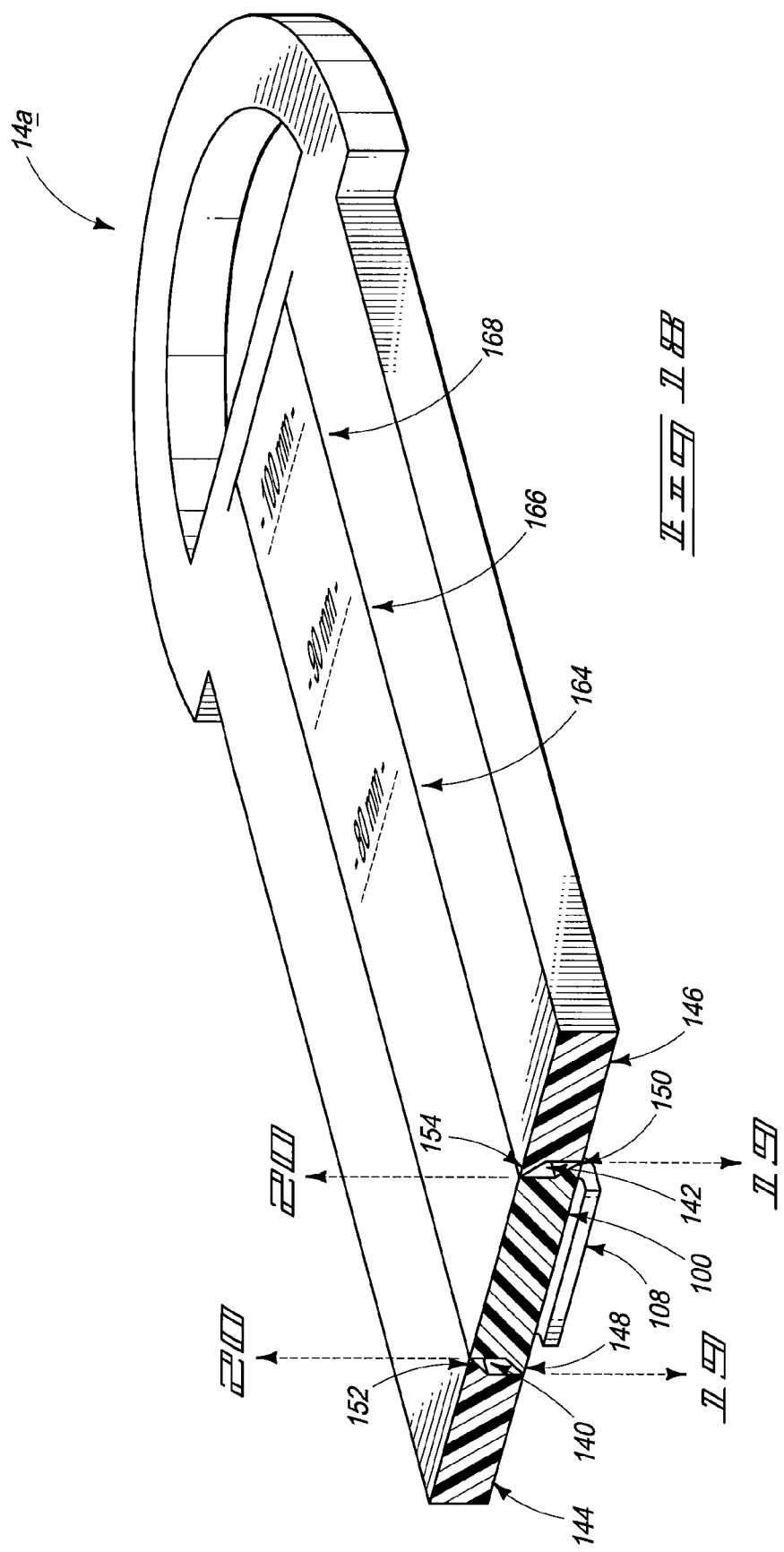

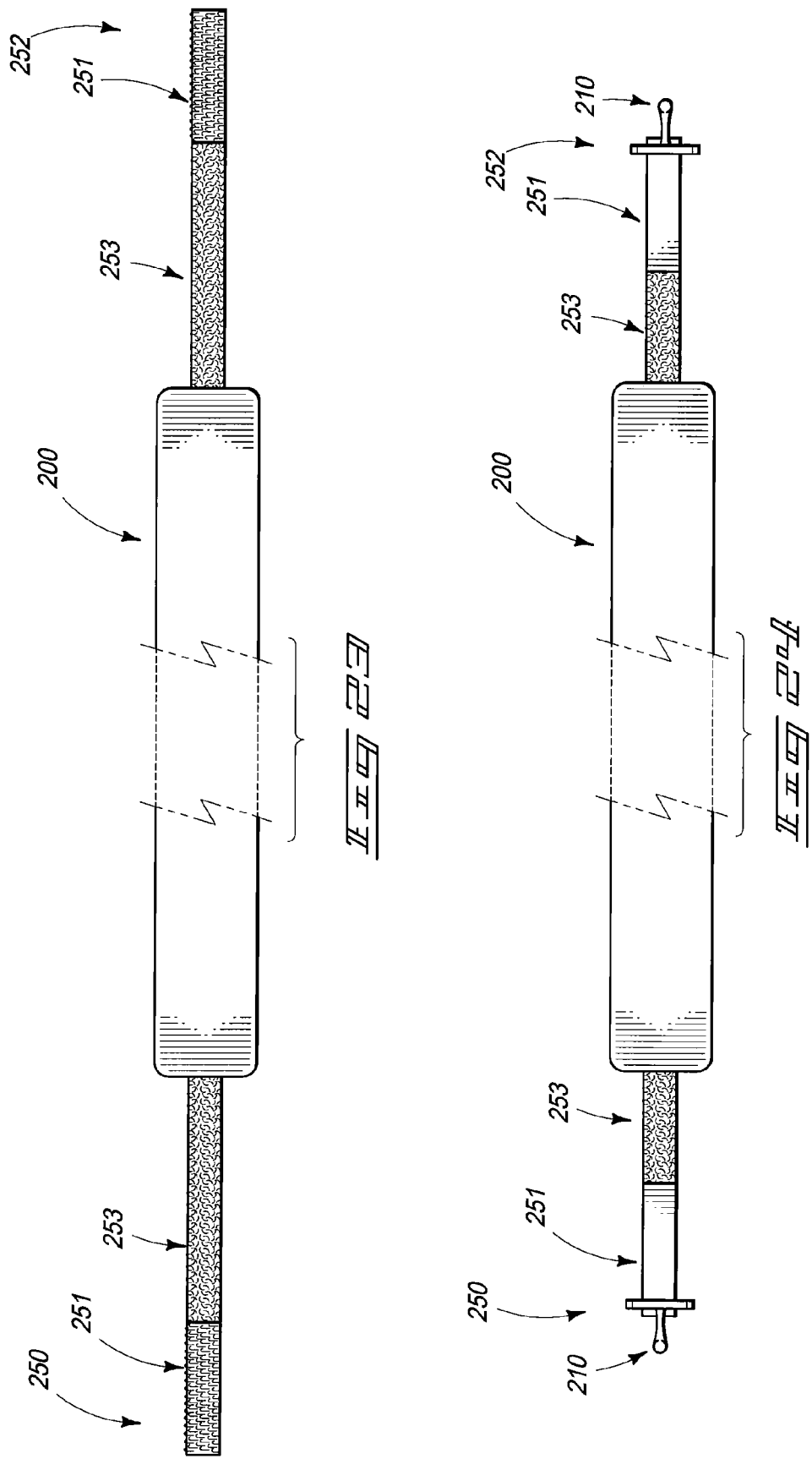

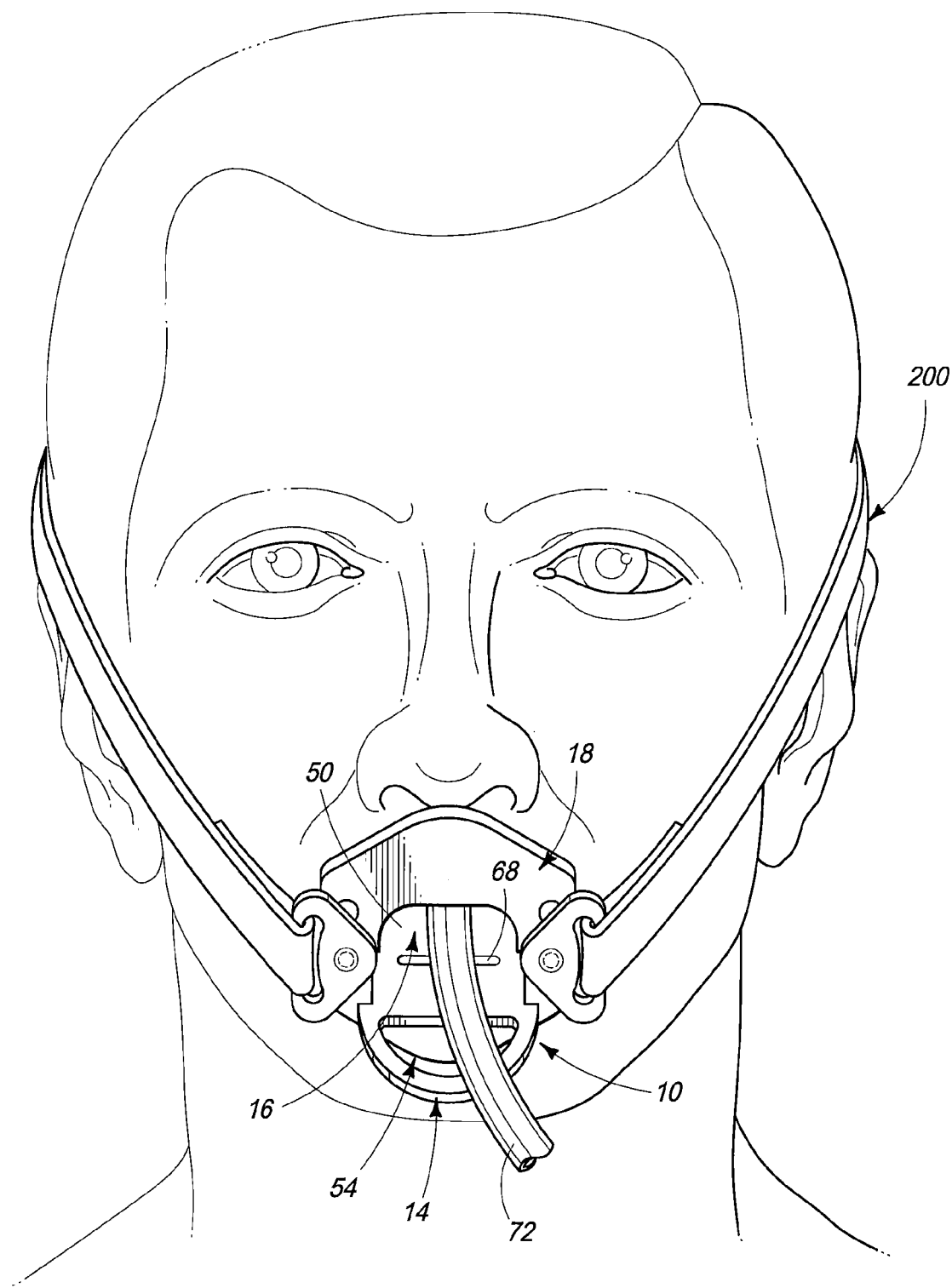

ADJUSTABLE ORAL AIRWAY DEVICES, AND ADJUSTABLE ORAL AIRWAY KITS

RELATED PATENT DATA

This application claims priority to U.S. Provisional Application Ser. No. 61/106,875, which was filed Oct. 20, 2008.

TECHNICAL FIELD

Adjustable oral airway devices, and adjustable oral airway kits.

BACKGROUND

Breathing difficulties may occur from severe trauma (such as trauma that may result from a vehicular crash), medical conditions, drug reactions, smoke inhalation, etc. Professional medical emergency response personnel (for instance, paramedics, medevac crews, firefighters, etc.) are thus trained to provide breathing assistance to injured persons. The breathing assistance may include ventilation and oxygenation (with oxygenation comprising administration of oxygen-enriched gas mixtures).

The administration of the ventilation and oxygenation may involve placement of a mask over the injured person's mouth, and/or insertion of a cannula into the injured person's mouth. An oral airway device is often placed in an injured person's mouth prior to utilization of the mask and/or cannula to prevent the soft tissues of the oropharynx (i.e., the part of the throat at the back of the mouth) from collapsing into and obstructing the airway. This can be particularly important if the injured person is unconscious, or in danger of becoming unconscious.

Commercially available oral airway devices often comprise a region that rests between the top and bottom teeth, together with a region having a distal curve (i.e., the blade) to provide support along the back of the palate. The region resting between the teeth may be configured to prevent clenching of the teeth on the tongue, as well as to prevent clenching of the teeth on medical structures (such as, for example, an endotracheal tube, a suction catheter, a fiberoptic laryngoscope, etc.) which may be passed into the oropharynx while the oral airway device is in place.

A problem for medical emergency response personal (e.g., so-called "first responders") is to find an appropriately sized oral airway device for the injured person (or to find appropriately-sized devices for more than one injured person if multiple injured persons are present at a site). If the wrong sized oral airway device is inserted into a person, it may fail to restrain soft tissues (if it is too small for a person's mouth and oropharynx), or may gag and/or choke the person (if it is too large for the person's mouth and oropharynx). Presently, medical emergency response personnel may carry a wide selection of oral airway device sizes and shapes in order to be adequately prepared for numerous different sizes of injured persons. However, stocking of a selection of different sizes of oral airway devices consumes valuable space in a tool kit. It is desired to develop improved oral airway devices that could be used for persons of different sizes, so that a single device could substitute for numerous different sizes of devices.

There has been some effort to develop adjustable oral airway devices. In theory, adjustable oral airway devices could eliminate the need for medical emergency response personnel to stock numerous different sizes of oral airway devices. However, the adjustable oral airway devices utilized by medical emergency response personnel should be suitable for rapid deployment under the stress of emergency situations, and under the awkwardness of the difficult environment conditions that may be encountered by the personnel in emergency situations. In practice, the presently available adjustable oral airway devices tend to be unsuitable for utilization by medical emergency response personnel under the adverse, and time-sensitive, conditions that may be encountered by such personnel. Accordingly, it is desired to develop improved adjustable oral airway devices.

SUMMARY

In one example embodiment, the invention includes an adjustable oral airway device. The device includes a bite block. The bite block has an opening extending therethrough, and has a longitudinal dimension along the opening. The device also includes a tongue deflector extending within the opening through the bite block. The tongue deflector is slideably engaged within the bite block; and is a strip of material comprising a straight region and a curved region. The straight region is at least as long as the longitudinal dimension of the bite block. Additionally, the device includes at least one locking mechanism configured for releasably retaining the tongue deflector in one of two or more predetermined positions within the bite block.

In another example embodiment, the invention includes another adjustable oral airway device. The device includes a bite block portion, a tongue deflector portion slideably engaged within the bite block portion, and at least one locking mechanism configured for releasably retaining the tongue deflector portion in one of two or more predetermined positions within the bite block portion. The device also includes a cannula-receiving region extending through the bite-block portion and along the tongue deflector portion.

In yet another example embodiment, the invention includes an adjustable oral airway kit. The kit includes a bite block. The bite block has an opening extending therethrough, and has a longitudinal dimension along the opening. The kit also includes a tongue deflector configured to extend within the opening through the bite block. The tongue deflector is configured to be slideably engaged within the bite block. The tongue deflector is a strip of material comprising a straight region and a curved region. The straight region is at least as long as the longitudinal dimension of the bite block. Additionally, the tongue deflector and bite block together comprise at least one locking mechanism configured for releasably retaining the tongue deflector in one of two or more predetermined positions within the bite block.

BRIEF DESCRIPTION OF THE DRAWINGS

FIG. 1 is a three-dimensional view of an example adjustable oral airway device.

FIG. 2 is an exploded view of the example adjustable oral airway device of FIG. 1.

FIG. 3 is a view of the bite block portion of the adjustable oral airway device of FIG. 1.

FIGS. 4 and 5 are a top view, and a side view, respectively, of the tongue deflector portion of the adjustable oral airway device of FIG. 1.

FIG. 6 shows side views of the example adjustable oral airway device of FIG. 1 at three different size adjustments.

FIG. 7 is a view of the adjustable oral airway device of FIG. 1 together with a cannula extended within an opening within the adjustable oral airway device.

FIGS. 9 and 10 are a top view, and a side view, respectively, of another embodiment of a tongue deflector portion of an adjustable oral airway device.

FIGS. 11-13 are a front view, cross-sectional top view, and cross-sectional side view, respectively, of an embodiment of a bite block portion that may utilized with the tongue deflector portion of FIGS. 9 and 10 to form an adjustable oral airway device. The view of FIG. 12 is along the lines 12-12 of FIGS. 11 and 13, and the view of FIG. 13 is along the lines 13-13 of FIGS. 11 and 12.

FIGS. 14-17 are cross-sectional side views showing the tongue deflector portion of FIGS. 9 and 10 engaged in the bite block portion of FIGS. 11-13 at various stages of adjustment of an adjustable oral airway device.

FIGS. 18-20 are views of the tongue deflector portion of FIG. 9 showing different stages of flexion of a biasing member of the tongue deflector portion. The views of FIGS. 18-20 are along a line labeled "18, 19, 20" of FIG. 9.

FIG. 23 shows a headband having hook and loop (e.g. VELCRO™) attachment regions at a pair of opposing ends.

FIG. 24 shows the headband of FIG. 23 after utilization of the hook and loop attachment regions to retain a pair of projecting stems to the headband.

FIG. 25 shows an adjustable oral airway device retained to a person's head with a headband.

DETAILED DESCRIPTION OF THE ILLUSTRATED EMBODIMENTS

Figure 8:
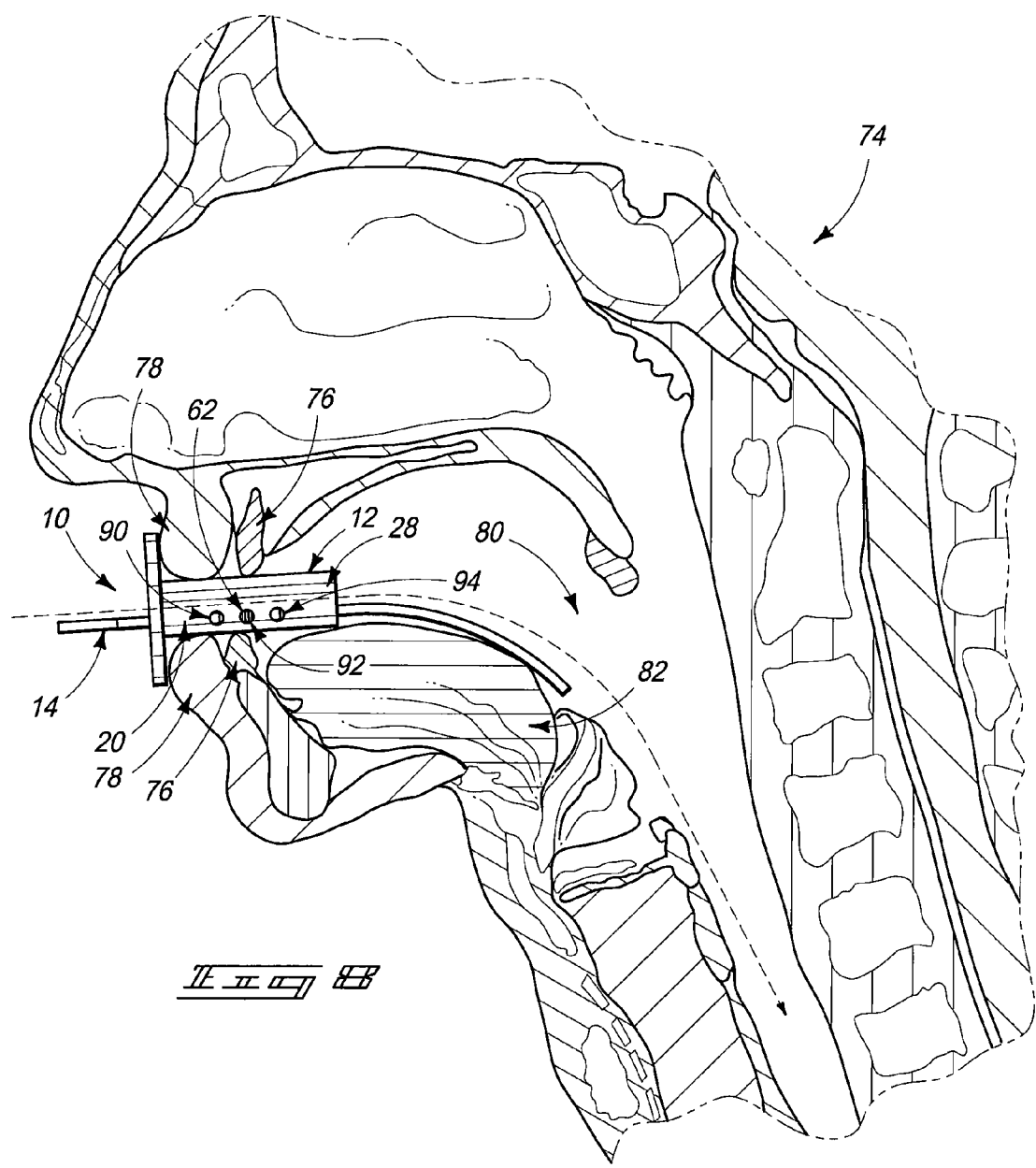
FIG. 8 is a cross-sectional view of a person's lower head and upper throat, showing the example adjustable oral airway device of FIG. 1 utilized to provide an oral airway for the person.

As discussed above in the "Background" section of this disclosure, a prior art problem exists with respect to conventional devices utilized for maintaining the oral airways of patients in an emergency applications. Specifically, the conventional devices are either non-adjustable so that numerous different sizes of devices must be carried by medical emergency response personnel to accommodate the different sizes of individuals that may be in need of aid; or, to the extent adjustable devices exist in the prior art, such tend to be awkward to utilize with the speed and efficiency desired in emergency applications.

In some embodiments, the invention includes adjustable oral airway devices that are convenient to utilize by medical emergency response personnel under the difficult conditions that they may encounter.

An example adjustable oral airway device 10 is shown in FIGS. 1 and 2. The adjustable oral airway device may be referred to as a Dual Air System™. The device 10 comprises two primary components—a bite block 12 and a tongue deflector 14. FIG. 1 shows the tongue deflector 14 slideably engaged within an opening 16 in the bite block 12; and FIG. 2 shows the tongue deflector 14 separate from the bite block 12. The tongue deflector and bite block may be completely separate components relative to one another (as shown); or in other embodiments (not shown) may be connected to one another through a tether or other suitable means. In some embodiments, the bite block 12 and tongue deflector 14 may be considered to be portions of the oral airway device 10; and accordingly may be referred to as a bite block portion and a tongue deflector portion, respectively.

The bite block 12 is shown in combination with the tongue deflector 14 in FIGS. 1 and 2, and is shown in isolation in FIG. 3. The bite block includes a planar surface 18 around the opening 16, and includes a bitable region 20 adjacent the planar surface 18. In operation, the bitable region is placed between the teeth of a person, and the planar surface 18 is outward of the lips of the person. The bite block comprises a material 15. In some embodiments, such material may comprise, consist essentially of, or consist of polypropylene, such as polypropylene approved for use in medical devices by the Environmental Protection Agency (EPA) and/or the Food and Drug Administration (FDA).

The opening 16 extends longitudinally through the planar surface 18 and through the bitable region 20 of the bite block 12.

The bite block may be considered to comprise a floor 22 beneath opening 16, a top 24 over the opening 16, and a pair of opposing sides 26 and 28 extending from the floor to the top along the sides of the opening 16.

The planar surface 18 may be considered to be a front surface of the bite block, and the bite block may be considered to comprise a back surface 19 in opposing relation to such front surface. The bite block has a longitudinal dimension 21 extending from the front surface 18 to the back surface 19; or, in other words, has a longitudinal dimension extending along opening 16. Such longitudinal dimension may be, for example, from about 4 centimeters to about 5 centimeters, in some embodiments. The bitable region 20 may have a length of from about 3.8 centimeters to about 4.8 centimeters in such embodiments.

The opening 16 has a height 23 between the floor 22 of the bite block and the top 24 of the bite block. A lower region of the opening 16 is a slot 30 configured for receipt of the tongue deflector 14, and an upper portion of the opening may be configured as a cannula-receiving region 32 (as explained in more detail below with reference to FIG. 7).

FIG. 1 shows the tongue deflector 14 received within the slot region 30 of opening 16, and shows that the cannula-receiving region 32 of the opening is over the tongue deflector. The cannula-receiving region may have any suitable shape, but it may be advantageous for there to be enough room in the cannula-receiving region to receive one or more cannulas, and to provide ample airspace adjacent the cannulas for ventilation to occur through the bite block while the one or more cannulas are in place. The cannula-receiving region may be substantially rectangular (as shown).

FIG. 1 shows that the cannula-receiving region 32 has a height 34 and a width 36. In some embodiments, the cannula-receiving region 32 may be at least three times as wide as it is tall. For instance, in some embodiments the height of the cannula-receiving region may be about 0.6 centimeters, and the width may be about two centimeters.

Bite block 12 comprises a pair of receptacles 200 and 202 extending through planar surface 18. Such receptacles may be utilized for connecting the bite block to a headband as discussed below with reference to FIGS. 22 and 25.

The bite block 12 has a plurality of cavities 40, 42 and 44 extending through the side 26 of the bite block. In some embodiments, the side 28 of the bite block will be a mirror image of the side 26 (as shown in FIG. 8), and accordingly will also have multiple cavities extending therethrough. In the shown embodiment, there are three cavities extending through the side 26. Each of the cavities represents a predetermined position where the tongue deflector may be locked into the bite block. The number of cavities may thus be chosen based upon the number of predetermined locking positions that are desired. There may be some applications in which is desired to have a large number of predetermined locking positions so that the location of the tongue deflector may be finely controlled. In other applications, it may be desired to have fewer predetermined locking positions so that the location of the tongue deflector is more coarsely controlled. It may be faster to adjust the tongue deflector to a desired location if there are fewer predetermined locking positions, but there will be a trade-off relative to the degree to which the adjustable oral airway device 10 may be tailored to specific mouth/throat sizes. There will generally be at least two predetermined locking positions associated with adjustable oral airway devices of the present invention.

Although the cavities 40, 42 and 44 are shown to extend entirely through the side 26 of bite block 12, in other applications the cavities may be dents formed along the interior of the wall (in other words, along opening 16) rather than being formed to extend entirely through the wall.

The tongue deflector 14 is shown in combination with the bite block 12 in FIGS. 1 and 2, and is shown in isolation in FIGS. 4 and 5. The tongue deflector comprises a material 50. Such material may be a pliable material, and in some embodiments may comprise, consist essentially of, or consist of polypropylene, such as polypropylene approved for use in medical devices by the Environmental Protection Agency (EPA) and/or the Food and Drug Administration (FDA).

The tongue deflector has a length 51, a width 53, and a thickness 55, as shown in FIGS. 4 and 5. In some embodiments, the length may be from about 11 centimeters to about 13 centimeters; the width may be from about 1.5 centimeters to about four centimeters; and the thickness may be less than or equal to about 0.2 centimeters.

A segment 52 of the length corresponds to a loop 54 configured to enable grasping by the fingers of a person operating the adjustable oral airway device 10. In some embodiments, segment 52 may have a length of from about one centimeter to about two centimeters. The loop 54 may be omitted in some embodiments.

FIG. 5 shows that the length 51 of the tongue deflector 14 may be considered to be sub-divided into three segments. One of the segments is the segment 52 discussed above as corresponding to loop 54. Another of the segments is a straight region 56, while the remaining segment corresponds to a curved region 58. The straight region 56 is utilized for adjustment of the tongue deflector location within the bite block 12, and the curved region 58 is utilized for retaining the tongue and/or other soft mouth/throat tissue of a patient. The straight region may be at least as long as the longitudinal dimension 21 of the bite block 12.

The tongue deflector 14 comprises a pair of deflectable protuberances 60 and 62 along the opposing sides of the tongue deflector. In operation, such protuberances engage within the cavities in the sidewalls of bite block 12 (for instance, cavities 40, 42 and 44 in the sidewall 26 of the bite block, and similar cavities in the opposing sidewall 28 of the bite block) to releasably retain the tongue deflector in the predetermined positions defined by the cavities. For instance, protuberance 60 may be seated within any one of the cavities 40, 42 and 44 to releasably retain the tongue deflector in a predetermined position.

The illustrated tongue deflector has marks 64, 66 and 68 which may be aligned to the planar surface 18 of the bite block 12 to identify to a user when the tongue deflector is engaged in a specific predetermined position. The tongue deflector has an end 70 which will be at the deepest location in a patient's throat during utilization of the adjustable oral airway device 10. The adjustable oral airway device may be provided with instructions, or with additional markings on one or both of the bite block and tongue deflector, which identify to the operator of the device the overall depth to which end 70 extends when the tongue deflector is in the predetermined positions identified by markings 64, 66 and 68.

Although three alignment markings 64, 66 and 68 are shown, in other embodiments there may be less than three alignment markings, and in yet other embodiments there may be more than three alignment markings. Generally, there will be at least two alignment markings corresponding to the at least two predetermined positions that the tongue deflector may be locked in relative to the bite block.

In the shown embodiment, tongue deflector 14 has a pair of slots 72 and 74 extending through the tongue deflector adjacent protuberances 60 and 62, respectively. The slots enable protuberances 60 and 62 to flex inwardly during adjustment of the tongue deflector within the bite block. The material 50 of the tongue deflector provides sufficient outward bias to the protuberances 60 and 62 so that the protuberances will lock within the cavities in the bite block when the protuberances are aligned with such cavities.

Although the illustrated tongue deflector has two protuberances, in other embodiments there may be only one protuberance utilized, and in yet other embodiments there may be more than two protuberances utilized.

The protuberances on the tongue deflector (i.e., the protuberances 60 and 62), together with the cavities in the bite block (for instance, cavities 40, 42 and 44) define a locking mechanism configured for releasably retaining the tongue deflector in one of two or more predetermined positions within the bite block.

FIG. 6 shows adjustable oral airway device 10 at three different size adjustments corresponding to the three different predetermined locations defined by cavities 40, 42 and 44. Specifically, a topmost orientation of the adjustable oral airway device shows the protuberance 60 of the tongue deflector 14 engaged within cavity 40, and thus shows the end 70 of the tongue deflector at the deepest predetermined location of the device 10. The next orientation down shows the protuberance 60 pulled into cavity 42, and thus shows the end 70 of the tongue deflector at a predetermined location that is less deep than that of the topmost orientation of device 10 in FIG. 6. The bottom orientation of the adjustable oral airway device shows the protuberance 60 engaged within cavity 44, and thus shows the end 70 of the tongue deflector at the shallowest predetermined location of the device 10.

FIG. 7 shows a cannula 72 extending through bite block 12 within the cannula-receiving region 32 of opening 16. FIG. 7 also shows that in some embodiments there may be a significant amount of space available within the cannula-receiving region 32 after a cannula it is inserted within such region. Such may enable multiple devices and/or cannulas to extend simultaneously through the bite block, and/or may enable ventilation to be provided through the bite block after one or more cannulas and devices are inserted through the cannula-receiving region.

FIG. 8 shows adjustable oral airway device 10 in operation, and specifically shows the device within the mouth and throat of a patient 74. The bitable region 20 of the bite block is between the teeth 76 of the upper and lower jaws of the patient, and also between the lips 78 of the patient. The device 10 has a large surface exterior of the patient's mouth, which can avoid having the device fall into the patient's mouth. The tongue deflector 14 extends into the upper throat 80 of the patient and holds down soft tissues 82 within the upper throat.

In practice, a mask (not shown) will typically be provided over the patient's mouth, and thus over the adjustable oral airway device 10. The mask may be used in bag valve mask ventilation. The opening 16 through the adjustable oral airway device 10 can provide, among other things, a route for ventilation between the mask and the patient's lungs, a path for a breathing tube to be inserted into a patient's mouth, a path for a flexible camera to be inserted into a patient's throat, and/or a path for a suction device to be inserted into a patient's mouth or throat.

One of the advantages of the invention is that if the patient 74 becomes conscious and is uncomfortable with the tongue deflector 14 and/or starts to gag on the tongue deflector, the tongue deflector may be retracted from the throat and pulled entirely out of the bite block, while leaving the bite block in place. Ventilation may continue to be provided through the opening 16 in the bite block after the tongue deflector is removed.

The view of bite block 10 in FIG. 8 is rotated relative to the view of FIGS. 1, 2 and 5, and accordingly side 28 is visible in FIG. 8. Side 28 is shown comprising cavities 90, 92 and 94 analogous to the cavities 40, 42 and 44 (FIG. 1) of side 26; and the protuberance 62 of tongue deflector 14 is shown engaged within the cavity 92.

The adjustable oral airway device 10 of FIGS. 1-8 comprises an embodiment of a locking mechanism in which protuberances along the side of a tongue deflector (specifically, the protuberances 60 and 62 shown in FIG. 4) engage within cavities in the sidewall of the bite block (specifically, the cavities 40, 42, 44, 90, 92 and 94 of FIGS. 1 and 8). In other embodiments, other locking mechanisms may be utilized.

FIGS. 9 and 10 illustrate a tongue deflector 14a of an example embodiment in which the locking mechanism includes a deflectable region 100 that extends downwardly from within a center of the tongue deflector. The tongue deflector 14a comprises the length 51 discussed above with reference to FIGS. 7 and 8, and comprises the segments 52, 56 and 58 of such length. Segment 52 is a handle, segment 56 is a straight region, and segment 58 is a curved region. In the shown embodiment, the deflectable protuberance 100 is within the straight region 56 of the tongue deflector.

The deflectable region 100 is along a length 102 of a deflectable material of the tongue deflector. Such length comprises a first end 104 where the deflectable material joins to the rest of tongue deflector 14a, and an opposing second end 106 which may be deflected downwardly from a central region of the tongue deflector. The second end 106 has a primary end surface 105 that is substantially orthogonal to an upper surface of the deflectable material of the tongue deflector. An engagement structure (which may be considered to be a deflectable protuberance) 108 extends downwardly from surface 105, and extends below a bottom surface 107 of the deflectable material. The engagement structure has an "L" shape, and specifically includes a lower base region 110 joining to a stem region 112. One surface of the stem region corresponds to the surface 105, and an opposing surface of the stem region includes a surface 109 that is angled relative to bottom surface 107. In operation, the engagement structure 108 corresponds to a protuberance that may be releasably retained in cavities formed along a bottom of a bite block.

FIGS. 12-13 illustrate an example bite block 12a which may be utilized in conjunction with the tongue deflector 14a of FIGS. 9 and 10.

Figure 11:
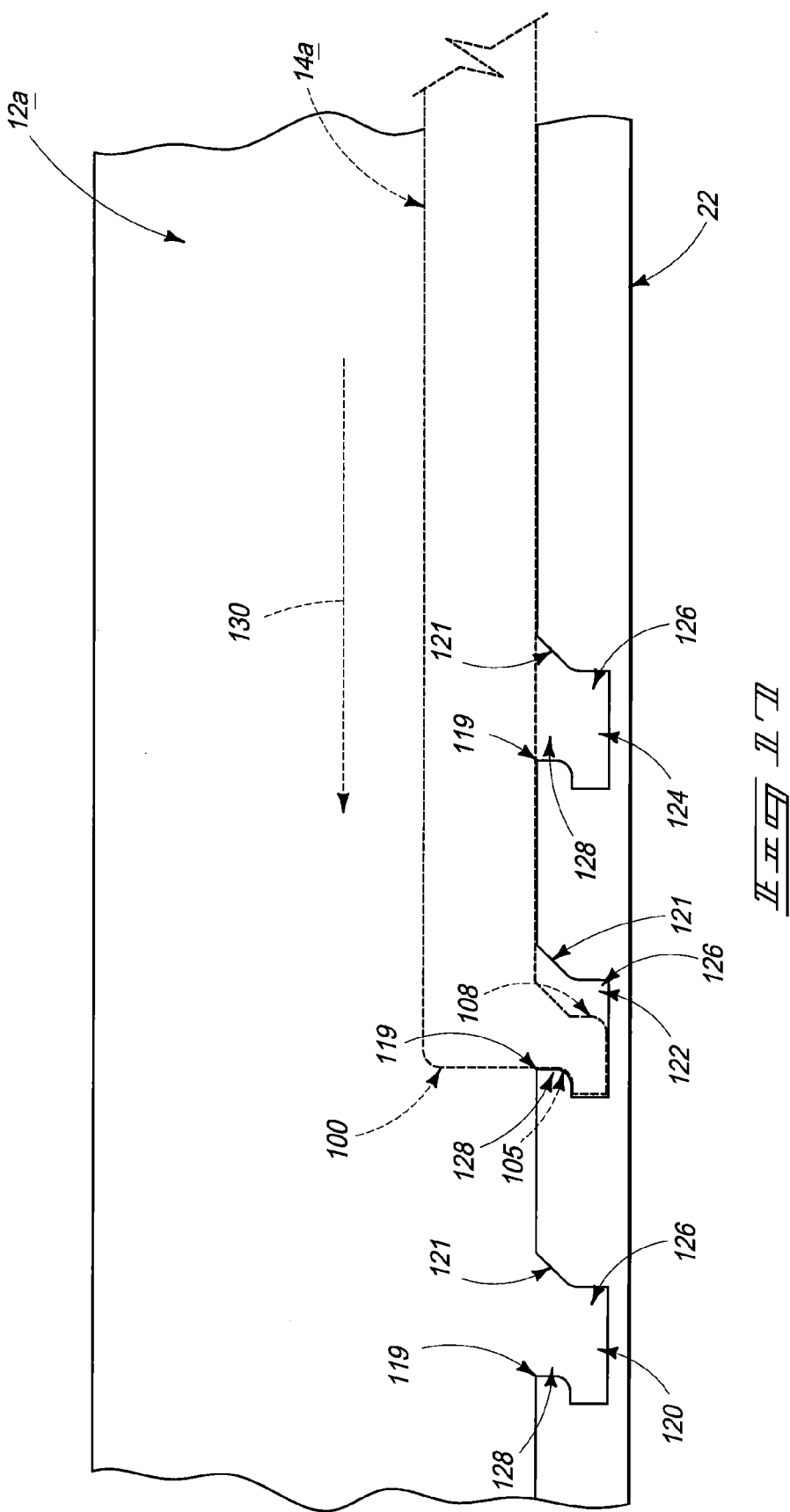

Bite block 12a includes the planar surface 18 discussed above in FIG. 1 with reference to bite block 12, and includes the bitable region 20 adjacent such planar surface. The bite block 12a also includes the opening 16, the floor 22 beneath the opening, the top 24 over the opening, and the opposing sides 26 and 28 extending from the floor to the top along the sides of the opening. However, in contrast to the bite block 12 of FIG. 1, the bite block 12a of FIGS. 11-13 does not include cavities 40, 42 and 44 along the sidewalls, but instead includes cavities 120, 122 and 124 extending into the floor 22.

The cavities 120, 122 and 124 are complementary to retaining structure 108, and accordingly comprise "L" shapes. Such "L" shapes include a base region 126 and a stem region 128. The stem region 128 includes a surface 119 that is substantially orthogonal to an upper surface 123 of the floor, and includes a surface 121 that is sloped (i.e., not orthogonal) relative to the upper surface 123 of the floor.

The tongue deflector 14a may comprise the same material 50 discussed above with reference to tongue deflector 14 of FIG. 1, and the bite block 12a may comprise the same material 15 discussed above with reference to the bite block 12 of FIG. 1.

FIGS. 14-17 illustrate utilization of deflectable region 100 relative to cavities 120, 122 and 124. The deflectable region 100 is shown in isolation from the rest of tongue deflector 14a to simplify the drawings, but it is to be understood that the deflectable region would be part of the tongue deflector 14a described in FIGS. 9 and 10.

FIG. 14 shows the deflectable region 100 sliding across a surface 123 along the floor 22 of bite block 12a, with a direction of movement of region 100 being indicated with arrow 130.

FIGS. 15 and 16 show the retaining structure 108 of deflectable region 100 falling into cavity 122 of bite block 12a. Directions of movement of region 100 are indicated by arrows 130 and 132.

FIG. 17 shows the retaining structure 108 of deflectable region 100 locking into cavity 122. More specifically, the surface 105 of the deflectable region 100 engages with the ridge 119 of the "L"-shaped cavity and precludes further movement of tongue deflector 14a along the direction indicated by arrow 130.

It is noted that the retaining structure 108 may be removed from within the cavity by pulling deflectable region 100 in a direction opposite to the direction of arrow 130. Specifically, the sloped region 121 of the cavity, in combination with the sloped surface 109 of deflectable region 100, enables retaining structure 108 to be lifted out of the cavity when the deflectable region 100 is pulled in a direction opposite to arrow 130. Thus, deflectable region 100 locks securely into one of the cavities 120, 122 and 124 when pushed in the direction of arrow 130, and may be released from within the cavity when pulled in a direction opposite to arrow 130.

The direction of arrow 130 may be referred to as a downstream direction (and specifically, such direction would be in a direction down a patient's throat in an orientation in which an adjustable oral airway device is utilized), and the direction opposite to arrow 130 may then be referred to as an upstream direction. Accordingly, deflectable region 100 of tongue deflector 14a may be considered to slide into cavities 120, 122 and 124 to preclude movement of the tongue deflector in the downstream direction, while enabling movement in the upstream direction. In operation, a mask over a patient's mouth may provide pressure on a tongue deflector to press the tongue deflector in the downstream direction and keep it locked within one of the cavities 120, 122 and 124.

In some embodiments, an adjustable oral airway device utilizing tongue deflector 14a and bite block 12a may be provided so that the deflectable region 100 is locked in the furthest downstream cavity (for instance, cavity 120 of FIGS.

14-17). Then an operator of the device may simply slide the tongue deflector upstream if it is desired to adjust the tongue deflector.

Figure 19:
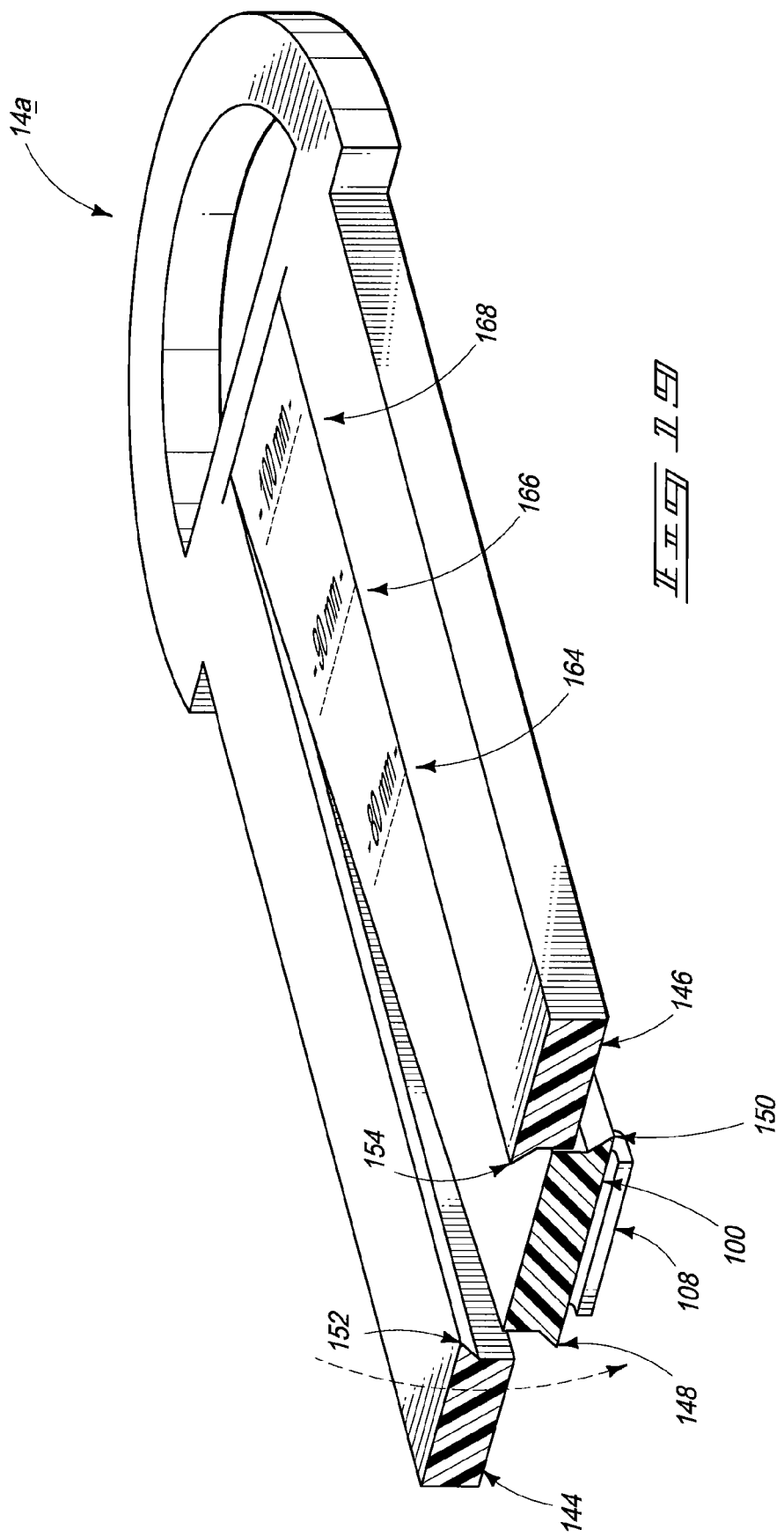
Figure 20:
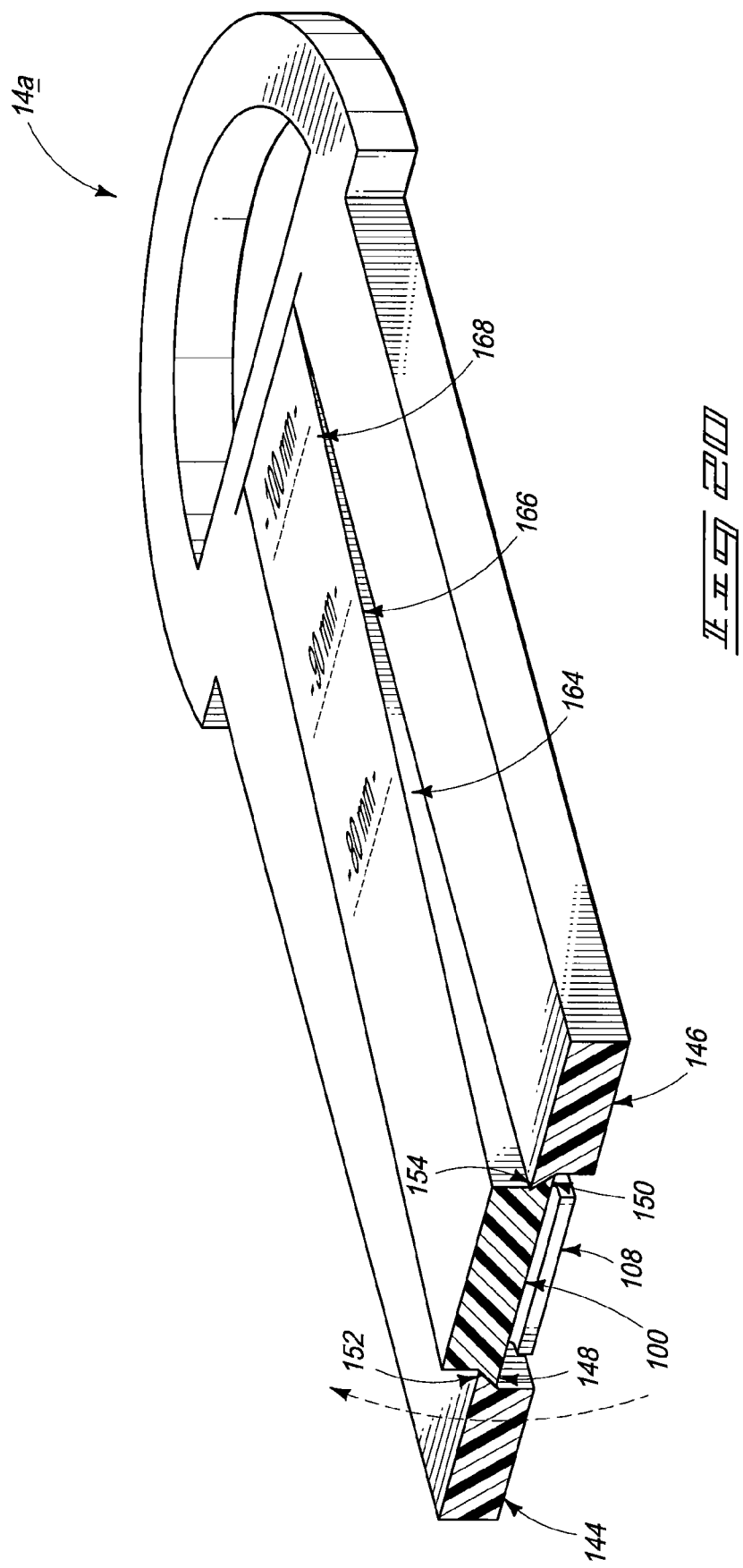

The deflectable region 100 has a bias that tends to push it into one of the cavities 120, 122 and 124 as the deflectable region passes across such cavity. The deflectable region may be passed over a cavity along the direction of arrow 130 if a counter-bias is provided to the deflectable region so that the deflectable region does not fall into the cavity. FIGS. 18-20 illustrate an embodiment in which an operator's fingers may be utilized to provide a counter-bias enabling the deflectable region to passed over cavities 120, 122 and 124 in the direction of arrow 130. FIGS. 18-20 show tongue deflector 14a with a cross-sectional cut along an edge of deflectable region 100. Such cross-sectional cut enables illustration of gaps 140 and 142 formed between lateral edges of the deflectable portion and adjacent edges of non-deflecting portions 144 and 146 of tongue deflector 14a. The gaps 140 and 142 result from removal of lateral sidewall regions of deflectable portion 100, and removal of lateral sidewall regions of non-deflecting portions 144 and 146. Remaining corners along the lateral edges of deflectable portion 100 form projecting points (or wings) 148 and 150, and similarly remaining corners along the lateral edges of non-deflecting portions 144 and 146 form projecting points (or wings) 152 and 154.

FIG. 19 shows deflectable region 100 biased to extend downwardly relative to non-deflecting portions 144 and 146. Such would lead to locking of deflectable region 100 into the cavities 120, 122 and 124 of FIGS. 14-17. Deflectable region 100 may have a natural downward bias induced by the combination of the choice of material of tongue deflector 14a and the shape of the deflectable region relative to the non-deflecting region. Alternatively, or additionally, a user of the tongue deflector may impart a downward bias on the deflectable region by utilizing finger pressure against such deflectable region.

FIG. 20 shows deflectable region 100 biased upwardly relative to non-deflecting portions 144 and 146. Such would enable the deflectable region to be passed across cavities 120, 122 and 124 of FIGS. 14-17 in the downstream direction of arrow 130. The user of the tongue deflector may impart the upward bias on the deflectable region by utilizing finger pressure against such deflectable region. In the shown embodiment, the points 148 and 150 of the deflectable region engage the points 152 and 154 of the non-deflecting portions to prevent the deflectable region from being popped up and over the non-deflecting portions. This may assist in alleviating problems that could occur during use of tongue deflector 14a that would render the tongue deflector inoperable. In some embodiments, points 148, 150, 152 and 154 may be omitted if it is found that there is little risk of problems occurring from users popping the deflectable region up and over the non-deflecting portions.

The tongue deflector 14a has markings 164, 166 and 168 similar to the markings 64, 66 and 68 discussed above with reference to FIGS. 4 and 5. Tongue deflector 14a is an example of an embodiment in which text is provided with the markings to indicate a depth to which a bottom end of the tongue deflector will extend into a patient's throat when such markings are aligned with a bite block.

Figure 21:
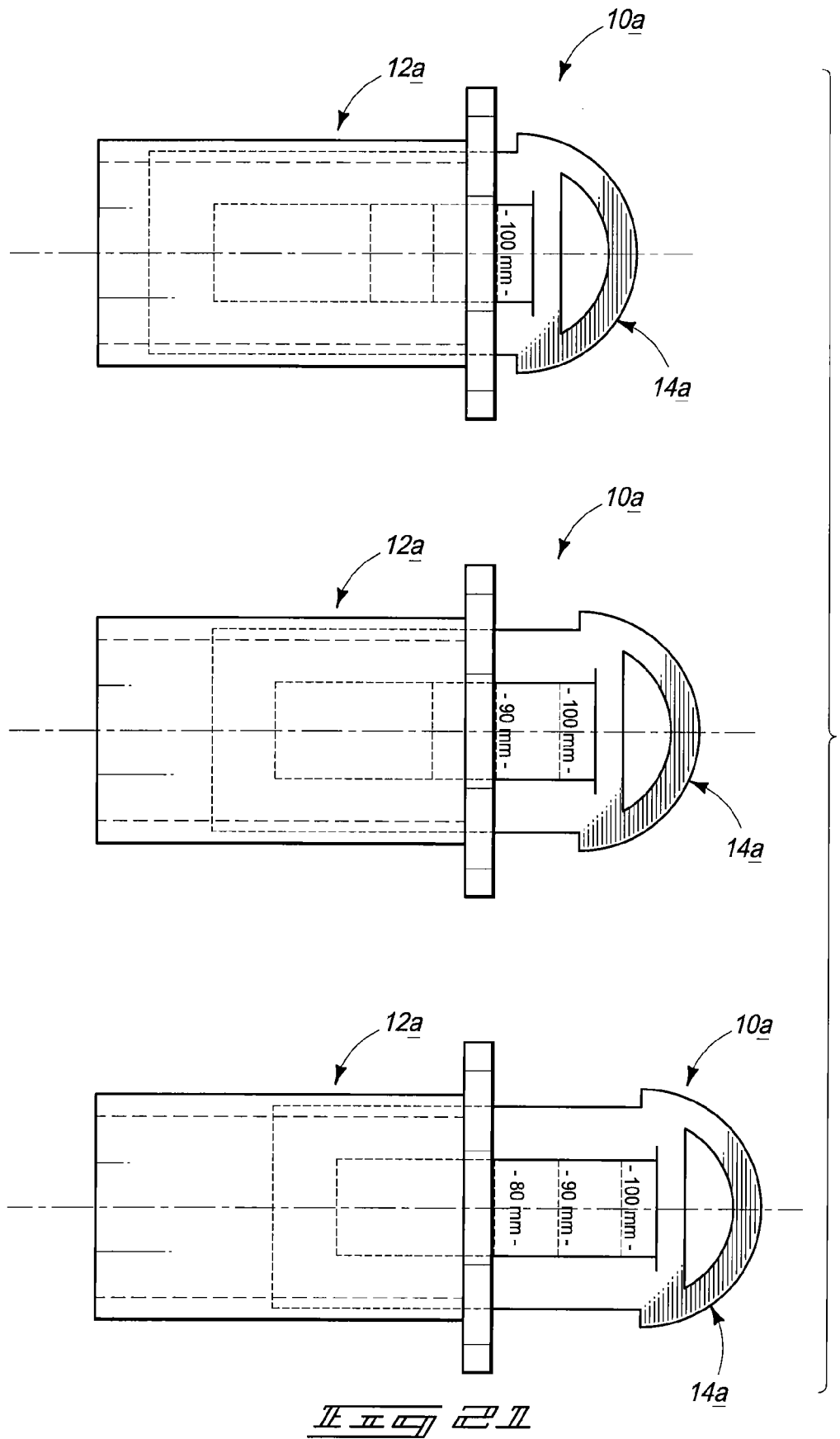
FIG. 21 shows top views of a portion of the example adjustable oral airway device of FIGS. 18-20 at three different size adjustments.

FIG. 21 shows an adjustable oral airway device 10a comprising the tongue deflector 14a in combination with the bite block 12a, and shows three specific predetermined positions that may be obtained by locking deflectable region 100 (FIGS. 14-17) into the various cavities 120, 122 and 124 (FIGS. 14-17).

Figure 22:
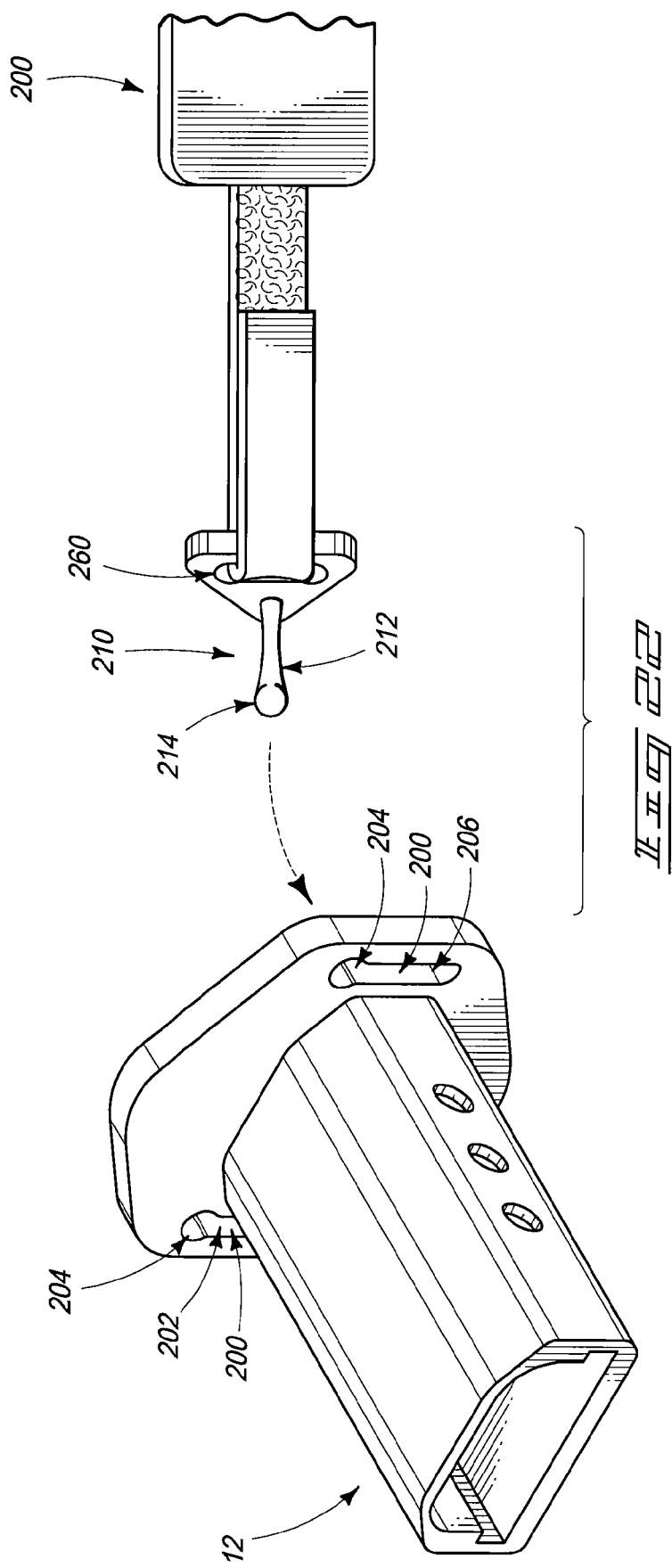
FIG. 22 shows a portion of a headband oriented for engagement with a slot in an example bite block portion of an adjustable oral airway device.

In some embodiments, adjustable oral airway devices may be configured to be retained on a patient's head with a headband or other suitable structure. FIG. 22 shows bite block 12, and a portion of a headband 200. The bite block comprises the receptacles 202 and 202. The receptacles each have a wide region 204 joining to a narrow slot region 206. The headband 200 has a pin 210 attached thereto. The pin has a narrow stem region 212 extending to a wide head region 214.

In operation, the wide head region 214 of stem 212 may be passed through the wide region 204 of receptacle 200, and then the stem 212 may be slid down into the narrow region 206 of the receptacle. Once the stem is slid down into the narrow region 206, the stem becomes locked in the receptacle due to the head 214 being too wide to pass out of the narrow region 206. The shown method of attachment of the headband to the bite block 12 may be accomplished quickly in an emergency situation.

The pin 210 may be connected to the headband with any suitable means. FIGS. 23 and 24 illustrate one embodiment for attaching the pin to the headband. FIG. 23 shows a headband 200 having a pair of opposing ends 250 and 252. Each of the ends has an outer region 251 and an inner region 253, with the outer and inner regions being complementary parts of a hook and loop (e.g. VELCRO™) system. Thus, the outer regions may be folded onto the inner regions, and will then connect with the inner regions through the hook and loop attachment system.

FIG. 24 shows pins to 10 joined on ends 250 and 252 by passing the ends of the headband through slots adjacent the pins (such slots are not visible in FIG. 24, but an example slot may be seen in FIG. 22 as a slot 260), and then folding the outer regions 251 onto the inner regions 253 to connect the outer regions to the inner regions and thereby retain the pins 210 to the headband 200. Such attachment may render the sizing of the headband to be adjustable by simply disconnecting the outer regions 251 from the inner regions 253, changing the amount of overlap of the outer regions over the inner regions, and then reattaching the outer regions to the inner regions.

FIG. 25 shows an adjustable oral airway device 10 retained on a patient's mouth with a headband 200. A cannula 72 extends into the opening 16 through the adjustable oral airway device. The tongue deflector 14 also extends within the opening 16, and the cannula is along an upper surface of the tongue deflector. The shown tongue deflector has a loop 54 to enable grasping by an operator, and has a marking 68 to provide a visual reference to the operator of how deep the end of the deflector is in the patient's mouth. A mask (not shown) may be provided over the patient's mouth and nose, and over the adjustable oral airway device, to assist in providing ventilation for the patient.

The various manipulations of the tongue deflector (for instance, movement of the tongue deflector within the bite block for sizing of the adjustable oral airway devices, removal of the tongue deflector from the bite block if a patient regains consciousness and becomes uncomfortable with the tongue deflector in his mouth, etc.) may be accomplished with limited manual dexterity, and thus may be accomplished with gloves on and/or with a loss of a fine motor skills that may occur in a stressful situation.

The adjustable oral airway devices shown herein may be particularly advantageous for utilization by professional medical emergency response personnel, in that the adjustable oral airway devices can take up less room in a toolbox than a large number of differently sized oral airway devices, and can be rapidly deployed under adverse and stressful conditions. However, the adjustable oral airway devices are not limited to emergency response applications, and may also be utilized in other applications in which breathing assistance may be administered, such as, for example, in hospitals (or other medical facilities) when patients are anesthetized during surgery.

In compliance with the statute, the subject matter disclosed herein has been described in language more or less specific as to structural and methodical features. It is to be understood, however, that the claims are not limited to the specific features shown and described, since the means herein disclosed comprise example embodiments. The claims are thus to be afforded full scope as literally worded, and to be appropriately interpreted in accordance with the doctrine of equivalents.

We claim:

1. An adjustable oral airway device, comprising:
a bite block; the bite block having an opening extending therethrough, and having a longitudinal dimension along the opening;
a tongue deflector extending within the opening through the bite block; the tongue deflector being slideably engaged within the bite block; the tongue deflector being a strip of material and comprising a straight region and a curved region; the straight region being at least as long as the longitudinal dimension of the bite block; and
the bite block and tongue deflector cooperatively defining at least one locking mechanism, the locking mechanism defining a plurality of different predefined positions for retaining the tongue deflector within the bite block, wherein the locking mechanism includes two or more cavities in a side of the bite block portion, and includes at least one deflectable protuberance along a side of the tongue deflector portion; the deflectable protuberance being configured to seat within the cavities to releasably retain the tongue deflector portion in said one of the predefined positions; wherein the locking mechanism further includes opposing cavities in another side of the bite block opposing the one side, the tongue deflector portion further including another deflectable protuberance opposing the one deflectable protuberance, the other protuberance configured to seat within the opposing cavities to releasably retain the tongue deflector portion in said one of the predefined positions.

2. The adjustable oral airway device of claim 1 wherein:
the bite block has a floor beneath the opening, a top over the opening, and a pair of opposing sides extending from the floor to the top along sides of the opening;
the opening has a height from the floor of the bite block to the top of the bite block, and comprises a lower slot region and an upper cannula-receiving region;
the tongue deflector is along the floor of the bite block and within the slot region of the opening; and
the cannula-receiving region of the opening is over the tongue deflector.

3. The adjustable oral airway device of claim 2 wherein the cannula-receiving region is at least three-times as wide as it is tall.

4. The adjustable oral airway device of claim 1 wherein the tongue deflector is a strip of pliable material.

5. The adjustable oral airway of claim 1 wherein the tongue deflector is a strip of polypropylene.

6. The adjustable oral airway device of claim 1 wherein the locking mechanism includes two or more ridges in a floor of the bite block adjacent the opening, and includes at least one deflectable protuberance within the straight region of the tongue deflector; the deflectable protuberance being configured to lock against the ridges to releasably retain the tongue deflector in said one of the predefined positions.

7. The adjustable oral airway device of claim 6 wherein the ridges are edges of cavities formed in the floor of the bite block, the cavities having "L" shapes with a lower base regions and an upper stem regions; and wherein the deflectable protuberance has an "L" shape complementary to the "L" shapes of the cavities and releasably seating within the cavities.

8. The adjustable oral airway device of claim 1 wherein the locking mechanism includes two or more cavities in a side of the bite block adjacent the opening, and includes at least one deflectable protuberance along a side of the tongue deflector; the deflectable protuberance being configured to seat within the cavities to releasably retain the tongue deflector in said one of the predefined positions.

9. An adjustable oral airway device, comprising:
a bite block portion;
a tongue deflector portion extending through the bite block portion and being slideably engaged within the bite block portion; the tongue deflector portion including a curved region extending outwardly of the bite block portion;
the bite block and tongue deflector cooperatively defining at least one locking mechanism, the locking mechanism defining a plurality of different fixed positions for retaining the tongue deflector within the bite block; and
a cannula-receiving region extending through the bite-block portion and along the tongue deflector portion.

10. The adjustable oral airway device of claim 9 wherein the cannula-receiving region has a height extending from the tongue deflector portion to the bite block portion, and has a width extending orthogonally to the height, and wherein the cannula-receiving region is at least three-times as wide as it is tall.

11. The adjustable oral airway device of claim 9 wherein the tongue deflector portion extends within a slot in the bite block portion.

12. The adjustable oral airway device of claim 9 wherein the locking mechanism includes two or more ridges in a floor of the bite block portion, and includes at least one deflectable protuberance within the tongue deflector portion; the deflectable protuberance being configured to lock against the ridges to releasably retain the tongue deflector portion in said one of the predefined positions.

* * * * *

UNITED STATES PATENT AND TRADEMARK OFFICE
CERTIFICATE OF CORRECTION

PATENT NO. : 8,297,275 B2
APPLICATION NO. : 12/409022
DATED : October 30, 2012
INVENTOR(S) : Daniel Dean Ogilvie and Beata Zawadzka Page 1 of 1

It is certified that error appears in the above-identified patent and that said Letters Patent is hereby corrected as shown below:

In the Specification:

Column 1, line 45 – Replace "response personal" with --response personnel--

Column 3, line 10 – Replace "may utilized" with --may be utilized--

Column 3, line 43 – Replace "emergency applications" with --emergency application--

Column 5, line 2 – Replace "which is" with --which it is--

Column 6, line 53 – Replace "cannula it is inserted" with --cannula is inserted--

Column 9, line 12 – Replace "passed over" with --pass over--

Column 10, line 28 – Replace "pins to 10" with --pins 210--

Column 10, line 59 – Replace "loss of a fine" with --loss of fine--

Signed and Sealed this
Twenty-fifth Day of June, 2013

Teresa Stanek Rea
*Acting Director of the United States Patent and Trademark Office*